US009585953B2

(12) United States Patent
Leenhouts et al.

(10) Patent No.: US 9,585,953 B2
(45) Date of Patent: Mar. 7, 2017

(54) IMMUNOGENIC COMPOSITIONS IN PARTICULATE FORM AND METHODS FOR PRODUCING THE SAME

(75) Inventors: Cornelis Johannes Leenhouts, Groningen (NL); Bert Jan Haijema, Groningen (NL); Maarten Leonardus van Roosmalen, Groningen (NL); Petrus Josephus Marie Rottier, Groningen (NL); Cornelis Alexander Maria de Haan, Groningen (NL); Berend Jan Bosch, Groningen (NL)

(73) Assignee: MUCOSIS B.V., Groningen (NL)

( * ) Notice: Subject to any disclaimer, the term of this patent is extended or adjusted under 35 U.S.C. 154(b) by 0 days.

(21) Appl. No.: 14/006,121

(22) PCT Filed: Mar. 22, 2012

(86) PCT No.: PCT/NL2012/050177
§ 371 (c)(1),
(2), (4) Date: Nov. 25, 2013

(87) PCT Pub. No.: WO2012/128628
PCT Pub. Date: Sep. 27, 2012

(65) Prior Publication Data
US 2014/0093532 A1 Apr. 3, 2014

(30) Foreign Application Priority Data

Mar. 22, 2011 (EP) ..................... 11159233

(51) Int. Cl.
| | | |
|---|---|---|
| A61K 39/385 | (2006.01) | |
| A61K 39/145 | (2006.01) | |
| A61K 39/155 | (2006.01) | |
| C07K 14/005 | (2006.01) | |
| A61K 47/48 | (2006.01) | |
| C12N 9/36 | (2006.01) | |
| A61K 39/12 | (2006.01) | |
| A61K 39/00 | (2006.01) | |

(52) U.S. Cl.
CPC ............ *A61K 39/385* (2013.01); *A61K 39/12* (2013.01); *A61K 39/145* (2013.01); *A61K 39/155* (2013.01); *A61K 47/4833* (2013.01); *A61K 47/48246* (2013.01); *C07K 14/005* (2013.01); *C12N 9/2462* (2013.01); *C12Y 302/01017* (2013.01); *A61K 2039/543* (2013.01); *A61K 2039/55505* (2013.01); *A61K 2039/6068* (2013.01); *C07K 2319/20* (2013.01); *C07K 2319/33* (2013.01); *C07K 2319/40* (2013.01); *C07K 2319/70* (2013.01); *C07K 2319/73* (2013.01); *C12N 2760/16122* (2013.01); *C12N 2760/16134* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

2010/0291147 A1* 11/2010 Baudoux et al. .......... 424/211.1

FOREIGN PATENT DOCUMENTS

| WO | 99/25836 | 5/1999 |
|---|---|---|
| WO | 02/074795 | 9/2002 |
| WO | 2009052573 A1 | 4/2009 |

OTHER PUBLICATIONS van Roosmalen et al. Mucosal vaccine delivery of antigens tightly bound to an adjuvant particle made from food-grade bacteria. Methods 38 (2006) 144-149.*
De Filette et al. An influenza A vaccine based on tetrameric ectodomain of matrix protein 2. J Biol Chem. Apr. 25, 2008;283(17)11382-7. Epub Feb. 5, 2008.*
Wang et al. Vaccination with a synthetic peptide from the influenza virus hemagglutinin provides protection against distinct viral subtypes. Proc Natl Acad Sci USA. Nov. 2, 2010;107(44):18979-84. Epub Oct. 18, 2010.*
GenBank: AAC33367.1, N-acetylmuramidase [Lactococcus lactis subsp. cremoris MG1363], Aug. 31, 1998.*
de Vries et al. The influenza A virus hemagglutinin glycosylation state affects receptor-binding specificity. 2010. Virology. 403:17-25.*
EP 1 754 972 A1. Date of publication: Feb. 21, 2007.*
Bosma et al., Novel Surface Display System for Proteins on Non-Genetically Modified Gram-Positive Bacteria, Applied and Environmental Microbiology, vol. 72, No. 1, p. 880-889 (2006).
Buist et al., Molecular Cloning and Nucleotide Sequence of the Gene Encoding the Major Peptidoglycan Hydrolase of Lactococcus lactis, a Muramidase Needed for Cell Separation, Journal of Bacteriology, vol. 177, No. 6, pp. 1554-1563 (1995).
Moeini et al., Lactobacillus acidophilus as a live vehicle for oral immunization against chicken anemia virus, Applied Microbiol Biotechnol, vol. 90, 77-88, (2011).

(Continued)

*Primary Examiner* — Nick Zou
(74) *Attorney, Agent, or Firm* — Hoffmann & Baron, LLP

(57) ABSTRACT

The invention relates to the field of immunology and vaccine development, in particular to the development of vaccines based on native antigen oligomers. Provided is an immunogenic composition in particulate form, comprising oligomers of a surface exposed polypeptide of pathogenic origin or tumor origin, or antigenic part thereof, said oligomers being bound non-covalently to a particulate carrier, and a pharmaceutically acceptable diluent or excipient. Also provided is a recombinant polypeptide comprising (A) an N- or C-terminal antigenic domain, comprising at least one surface exposed polypeptide of pathogenic or tumor origin, or antigenic part thereof, the antigenic domain being fused to (B) an oligomerization domain (OMD), said oligomerization domain being fused via (C) a linker domain to (D) a peptidoglycan binding domain (PBD) consisting of a single copy of a LysM domain capable of mediating the non-covalent attachment of the polypeptide to a non-viable bacterium-like particle (BLP) obtained from a Gram-positive bacterium.

25 Claims, 13 Drawing Sheets

(56) References Cited

OTHER PUBLICATIONS

Figure 1:
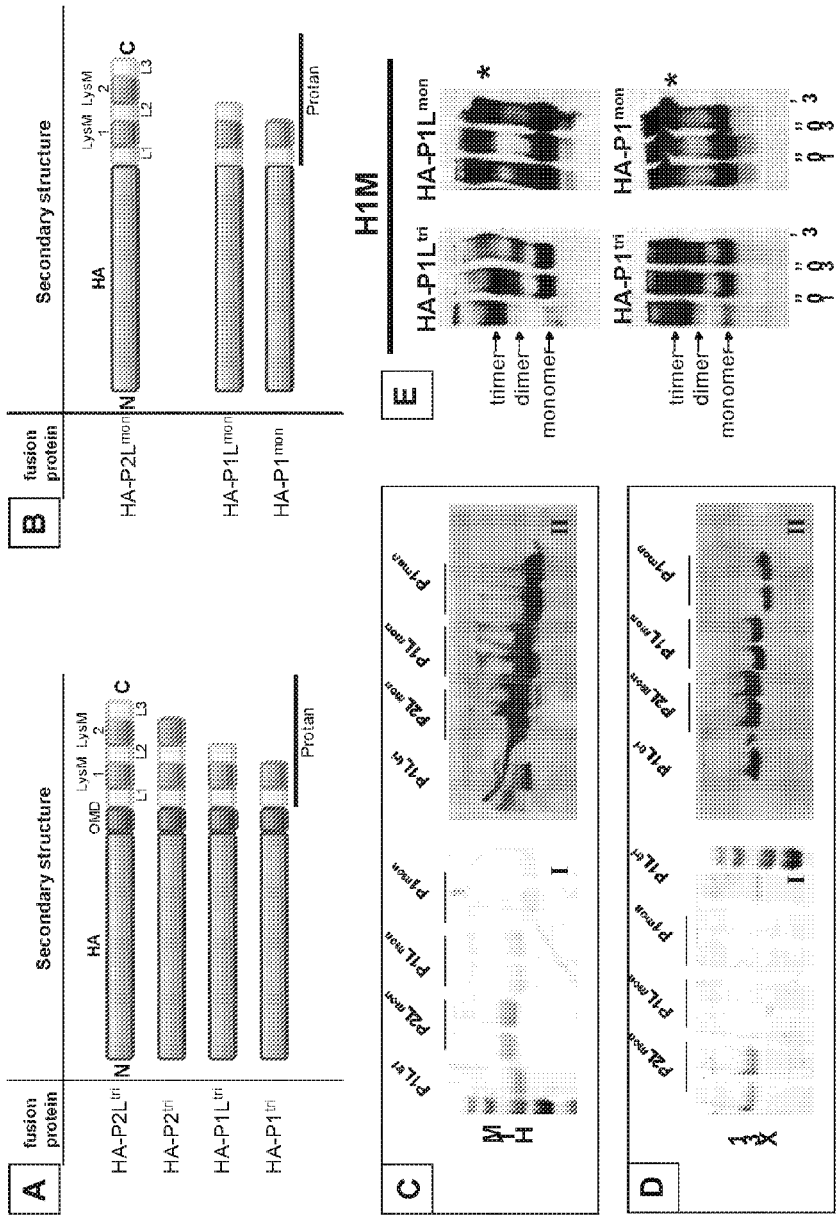

Raha et al., Cell surface display system for Lactococcus lactis: a novel development for oral vaccine, Appl. Microbiol Biotechnol, vol. 68, pp. 75-81 (2005).
Roosmalen et al., Mucosal vaccine delivery of antigens tightly bound to an adjuvant particle made from food-grade bacteria, Methods, vol. 38, pp. 144-149 (2006).

* cited by examiner

IMMUNOGENIC COMPOSITIONS IN PARTICULATE FORM AND METHODS FOR PRODUCING THE SAME

This application is the U.S. National Phase of, and Applicants claim priority from, International Application No. PCT/NL2012/050177 filed Mar. 22, 2012, which claims priority from European Application No. EP 11159233.3 filed Mar. 22, 2011, each of which are incorporated herein by reference.

BACKGROUND OF THE INVENTION

The invention relates to the field of immunology and vaccine development, in particular to the development of vaccines based on native antigen oligomers.

Many surface exposed proteins of pathogens and tumour cells are functional as oligomers. Examples for pathogens are for example, influenza virus hemagglutinin (HA) which occurs in virions as a homotrimer, and neuraminidase (NA) as a homotetramer. Also, the human immunodeficiency virus (HIV) glycoproteins gp140/gp120 is a homotrimer in its active form. Likewise, the respiratory syncytial virus (RSV) glycoproteins G and F occur in virions as tetrameric and trimeric homo-oligomers, respectively. Likewise, coronavirus spikes consist of homotrimers as is the case for the human respiratory coronaviruses and for SARS coronaviruses. Examples for tumour cells are for example, receptor tyrosine kinases (RTKs). RTKs are the high-affinity cell surface receptors for many polypeptide growth factors, cytokines, and hormones. Growth factor receptors include: epidermal growth factor receptor, fibroblast growth factor receptors and platelet-derived growth factor receptor. Hormone receptors include: androgen receptor and estrogen receptor. An example of the epidermal growth factor receptor (EGFR) is the ErbB protein family of four structurally related RTKs. The four members of the ErbB protein family are capable of forming homodimers, heterodimers, and possibly higher-order oligomers upon activation by a subset of potential growth factor ligands. ErbB-1 is overexpressed in many cancers. The platelet-derived growth factor receptor (PDGF) family consists of PDGF-A, -B, -C and -D, which form either homo- or heterodimers (PDGF-AA, -AB, -BB, -CC, -DD). The four PDGFs are inactive in their monomeric forms. Such oligomeric proteins of pathogens and tumour cells are often involved in the pathogenicity and immunogenicity of the disease-causing entity (viruses, bacteria, parasites) or in cancer development, respectively, and are therefore important targets for vaccine development.

However, during vaccine preparation the integrity and, hence, the antigenicity of these oligomeric structures may be negatively affected e.g. if the manufacturing process involves inactivation of the pathogen. Alternatively, the oligomeric status of the antigen may not be obtained due to the production process used for the manufacturing of (re-combinant) subunit vaccines. In both cases, this may result in aggregation or dissociation into a monomeric and/or misfolded state of the proteins.

Conformational epitopes embedded in the quaternary structures of oligomers may critically contribute to immunogenicity (Weldon et al. PLoS One 5 [2010], pii: e12466). Du et al. (Virology 395 [2009], 33-44) e.g. found that immunization of rabbits provided no evidence that trimerized gp140 constructs induced significantly improved neutralizing antibodies to several HIV-1 pseudoviruses, compared to gp140 lacking a trimerization motif. On the other hand, Grundner et al. (Virology 331 [2005], 33-46) showed that immunization of rabbits with the gp140 trimer elicited neutralizing antibodies of greater potency and breadth than did either gp120 or solid-phase proteoliposomes containing a cleavage-defective Env. Also Wei et al. (J. Virol. 82 [2008], 6200-6208) demonstrated that trimeric viral spikes serve as the optimal protein immunogens to elicit neutralizing antibodies against H5N1 isolates. Of other note, Bosch et al. (J. Virol. 84 [2010], 10366-10374) provided evidence that the combination of soluble trimeric HA and tetrameric NA of pandemic swine-origin 2009 A(H1N1) influenza virus in the presence of adjuvant provides protection against infection in ferrets.

Therefore, it is conceivable that the presence of native oligomeric protein antigens in vaccines is pivotal for their protective capacity. In many instances, oligomerization is determined by a subdomain having strong oligomerization properties. Also in many cases, such oligomerization subdomain of vaccine antigens is embedded in a membrane. To enable oligomerization of vaccine subunit antigens in the absence of a lipid environment, native oligomerization subdomains can be substituted by a heterologous coiled-coil motif with similar conformation-inducing properties. Examples of such motifs that have been successfully applied to obtain native oligomeric protein structures are a 32-amino-acid form of the GCN4 transcription factor (GCN), a 27-amino-acid trimerization domain from the C-terminus of bacteriophage T4 fibritin (T4F), and a soluble trimerization domain of chicken cartilage matrix (CART) protein (Selvarajah et al., AIDS Res. Hum. Retrovir. 24 [2008] 301-314; Yang et al., J. Virol. 74 [2000], 5716-5725; Yang et al., J. Virol. 76 [2002], 4634-4642).

Hence, technology to produce native oligomeric subunit vaccine antigens is available. Nevertheless, it is known that soluble subunit vaccine antigens are poorly immunogenic in general and need adjuvants and/or a particulate carrier system in order to raise robust immune responses. In the recent past there has been a growing interest in the development of novel non-replicating antigen presentation systems in order to increase the immunogenicity of antigens that could be used as vaccines. Many of these systems are designed in such a way to present the antigen as a polyvalent particulate structure. Some of the well appreciated examples are those of hepatitis B virus core and surface proteins genetically fused to foot-and-mouth disease virus (FMDV) (Clarke et al., Nature 330 [1987], 381-384) and HIV (Michel et al., Proc. Natl. Acad. Sci. USA 85 [1988], 7957-7961; Schlienger et al., J. Virol. 66 [1992], 2570-2576) antigens; the development of Ty virus like particles (VLPs) as antigen carriers (Adams et al., Nature 329 [1987], 68-70) where antigens are genetically fused to the C-terminus of the TYA gene encoded protein of the yeast retro-transposon Ty to form hybrid Ty-VLPs, parvovirus like particles (Miyamura et al., Proc. Natl. Acad. Sci. USA 91 [1994], 8507-8511). These technologies ensure that the antigen in question is presented in multiple copies in relatively large particles.

Other known particulate carriers for antigens are virosomes which are complexes composed of lipids and at least one viral envelope protein, produced by an in vitro procedure. The lipids are either purified from eggs or plants or produced synthetically, and a fraction of the lipids originates from the virus providing the envelope protein. Essentially, virosomes represent reconstituted, empty virus envelopes devoid of the nucleocapsid including the genetic material of the source virus(es). Virosomes are not able to replicate but are pure fusion-active vesicles. Known virosomes for use as antigen carrier include virosomes termed immunopotentiating reconstituted influenza virosomes (IRIVs). IRIVs are spherical, unilamellar vesicles with a mean diameter of 150 nm and comprise a double lipid membrane, consisting essentially of phospholipids, preferably phosphatidylcholines (PC) and phosphatidylethanolamines (PE). IRIVs may contain the functional viral envelope glycoproteins HA and NA intercalated in the phospholipid bilayer membrane. The biologically active HA does not only confer structural stability and homogeneity to virosomal formulations but also significantly contributes to the immunological properties by maintaining the fusion activity of a virus.

Although these known technologies can provide particulate carriers which enhance the immunological properties of a vaccine preparation, the methodologies are typically rather cumbersome and require specialized equipment and personnel. In addition, the use of viral material as carrier is preferably to be avoided. Furthermore, none of the existing technologies have been reported to be applied successfully in the manufacture of native oligomeric subunit vaccines.

Whereas it is known in the art (see e.g. WO 02/101026) to present an antigen to the immune system by fusion to a peptidoglycan binding sequence and attachment to particles derived from a Gram-positive bacterium, this particulate carrier technology has thus far only been described and applied in relation to the presentation of monomeric antigens.

WO 99/25836 and Bosma et al. (Appl. Environ. Microbiol. 72 [2006], 880-889) teach that one LysM domain suffices to mediate antigen obtain binding to Gram-positive microorganisms and/or peptidoglycan microparticles (BLPs, formerly called GEMs). This approach was for example followed by Raha et al. (Appl. Microbiol. Biotechnol 68 [2005], 75-81) and Moeini et al. (Appl. Microbiol. Biotechnol 90 [2011], 77-88). However, antigen binding via only a single LysM domain is rather limited (Bosma et al.) and not very stable, as shown by Raha et al. (FIG. 6) who determined that approximately 30 to 45% of the initially bound antigen is lost after a storage period of 5 days. In agreement with that observation, Moeini et al. shows in FIG. 6 that approximately 40% of the antigen bound through a single LysM domain is lost after a storage period of 5 days.

The successful manufacturing of vaccines requires long term storage for several months or sometimes even for years. The use of a single LysM binding domain results not only in low binding yields (Bosma et al.) but also in low stability of the bound antigens (Raha et al., Moeini et al.). Thus, this approach is unsuitable for an economically viable vaccine production process for BLP-based vaccines, which require optimal loading of antigens to the particles, i.e. high loading yields, in combination with antigens that remain stably bound over a prolonged period.

Prior to the present invention, the commonly held view to improve the efficacy and stability of antigen binding was to increase the number of LysM domains. In fact, it was demonstrated in the art that consecutive LysM domains in a single construct (2 to 3 domains in line; in cis/intramolecular) provides the most optimal and stable binding. See FIG. 3 of Bosma et al., showing a steep increase in binding affinity by the addition of a second LysM domain, and the level was even higher than that of wild-type AcmA comprising 3 LysM domains in cis. However, the present inventors observed that the approach of using two (or more) consecutive LysM domains in a single construct does not yield the expected results in case of oligomeric antigen binding. This is because the LysM tandem repeat mediates such a strong binding that not only functional oligomers but also non-functional monomers are bound to the carrier. The presence of non-functional monomers in vaccines is highly undesirable because such a heterogeneous complex makes it more difficult and cumbersome to characterize formulated vaccines. Furthermore, non-functional monomers containing LysM tandem repeats compete strongly with the functional oligomers for the available binding sites on the BLPs. Most importantly, non-functional monomers in vaccines may impose a health risk for the vaccinated subject since it is known in the art that non-functional, improperly folded antigens can induce a detrimental immune response.

The inventors therefore aimed at providing stable native oligomeric subunit vaccines not only having improved immunogenicity but which can also be produced in a relatively easy and economically attractive manner. In particular, it was an object to increase the safety and efficacy of (current) vaccines in a simple and reliable manner while avoiding the use of pathogenic or otherwise unsafe starting materials.

DESCRIPTION OF THE INVENTION

Figure 2A:
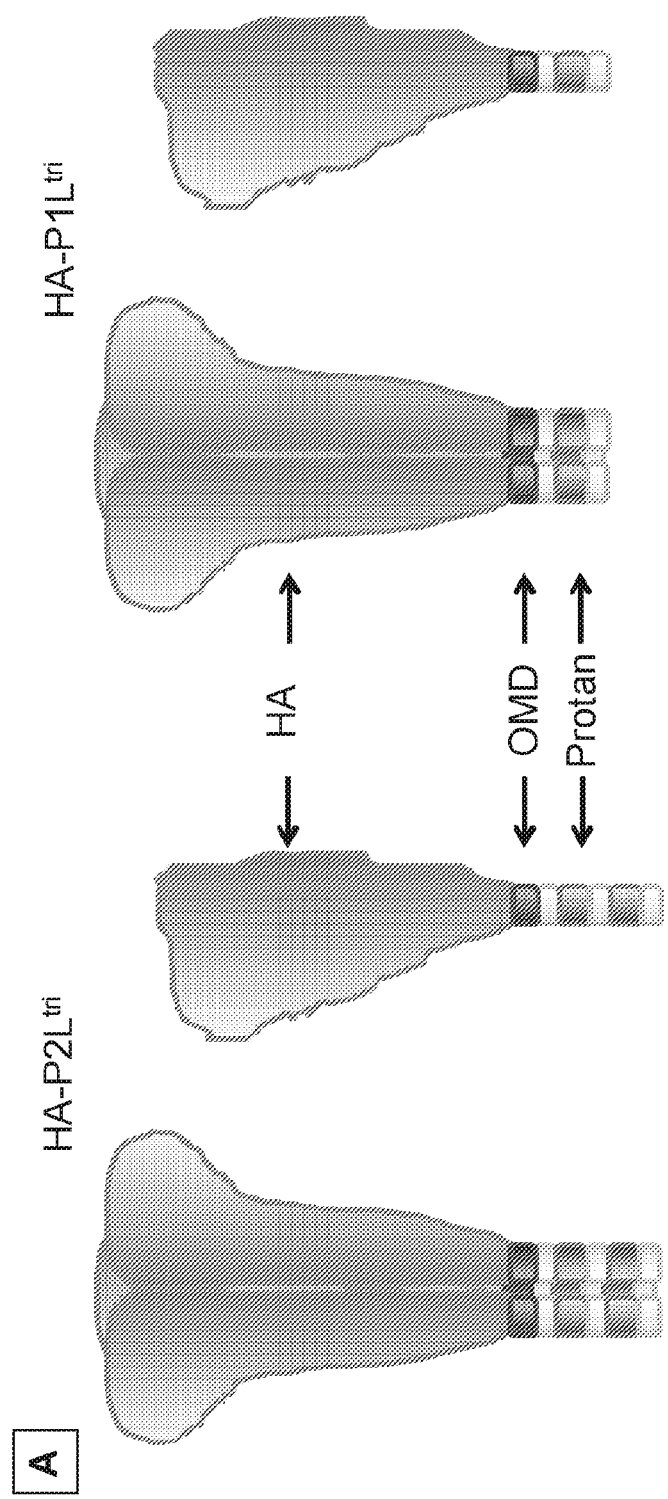
Figure 2B:
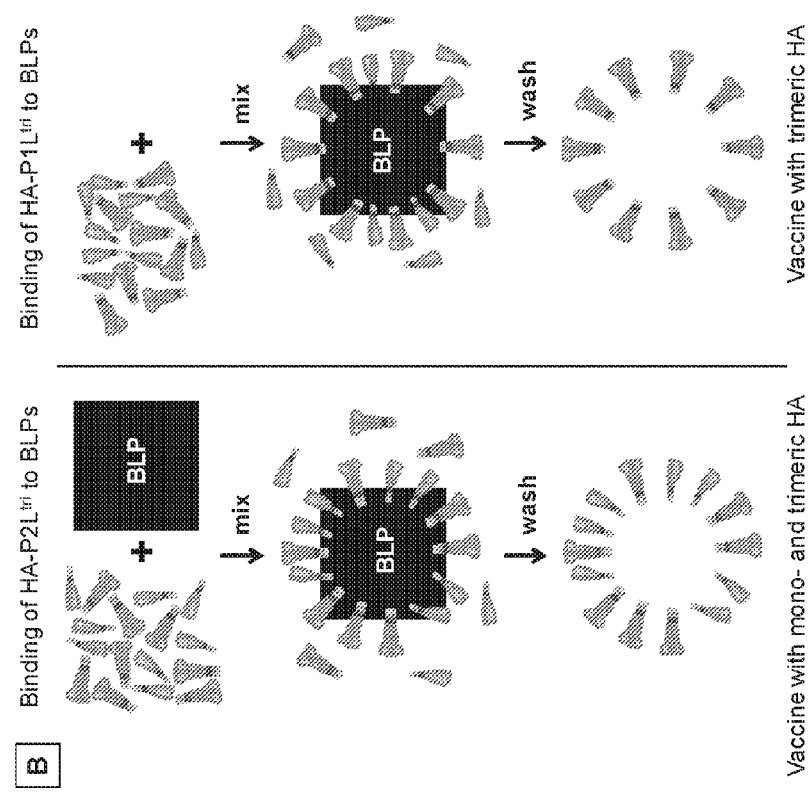

It was surprisingly found that preferential binding of functional oligomers is obtained if antigens are fused to only a single LysM domain in combination with an oligomerization domain (OMD) (see FIG. 2). The combination of a single LysM domain fused via a linker sequence to an oligomerization domain minimizes the presence of unwanted non-functional improperly folded antigens in the vaccine, thereby enhancing the safety of the vaccine. Moreover, vaccines with BLP bound oligomers made from antigens that contain a single LysM domain and an OMD showed a high stability upon prolonged storage (see FIG. 5).

Without wishing to be bound by theory, it appears that the addition of the OMD enhances the binding characteristics of the single LysM domains, supposedly through intermolecular interactions of multiple molecules in the oligomer, to a similar level as is achieved through intramolecular interactions for multiple LysM domains in a single molecule. Presumably, when using a single LysM domain, in a mixture of functional oligomeric antigens and non-functional monomers, the oligomers bind preferentially to the BLPs because the single LysM domain in a monomer configuration has only weak BLP binding properties. On the other hand, the single LysM domains of each individual molecule in an oligomeric configuration have been brought into such close proximity (in trans) of each other (by virtue of the OMD) that a high binding functionality is obtained which is comparable to two or more LysM domains in a single molecule. Hence, the surprising insight underlying the present invention is that a single LysM domain per subunit when assembled into one oligomeric molecule by the use of an OMD allows for a preferential binding of the desired native oligomeric antigen, which is not possible if the OMD is omitted or two or more (intramolecular) LysM domains are used.

The present finding also enables the selective binding of the desired native oligomers from a mixture solution of oligomers and monomers, since monomers with a single LysM domain show very poor binding and oligomers with a single LysM domain bind very efficiently. This selective binding of oligomers from a mixed solution of oligo- and monomers is not possible if two or more LysM binding domains are used, since efficient binding is in those cases observed for both mono- and oligomers, or monomers even bind more efficiently.

As an illustration, in order to bind oligomeric subunit antigens in their native conformation to the particles, the influenza HA and NA antigens and the respiratory syncytial virus F antigen were each fused to the GCN4 domain and via a linker to a peptidoglycan binding domain (Protan) (from N- to C-terminus: HA-GCN4-Protan and Protan-GCN4—NA; F-GCN4-Protan). The HA-GCN4-Protan, F-GCN4_Protan and Protan-GCN4-NA fusions produced in human embryonic kidney (HEK293) cells rendered trimers, trimers and tetramers, respectively, that were also able to bind to said peptidoglycan carrier particles (BLPs). Similar productions were done using Chinese hamster ovary cells and insect cells. Functionality of the HA oligomer immobilized on the particles was demonstrated in a haemagglutination assay performed with said particles. Immunogenicity of the said particles loaded with said HA oligomer was demonstrated in a mouse model. Immunogenicity of the particles loaded with F oligomer was demonstrated in a mouse model and efficacy was demonstrated in a cotton rat model.

The invention accordingly relates to a recombinant polypeptide comprising:

A) an N- or C-terminal antigenic domain, comprising at least one surface exposed polypeptide (e.g. of pathogenic or tumour cell origin) or antigenic part thereof, the antigenic domain being fused to
B) an oligomerization domain (OMD), said oligomerization domain being fused via
C) a linker domain to
D) a peptidoglycan binding domain (PBD) consisting of a single copy of a LysM domain capable of mediating the non-covalent attachment of the polypeptide to a peptidoglycan carrier particle being a non-viable bacterium-like particle (BLP) obtained from a Gram-positive bacterium, and wherein the polypeptide as a whole contains only a single copy of a LysM domain.

In particular, the invention provides an immunogenic composition in particulate form, comprising:

i. a non-viable bacterium-like particle (BLP) obtained from a Gram-positive bacterium as particulate carrier;
ii. oligomers of a recombinantly produced polypeptide attached non-covalently to said BLP, wherein the recombinant polypeptide comprises:
   A) an N- or C-terminal antigenic domain, comprising at least one surface exposed polypeptide of pathogenic or tumour origin, or antigenic part thereof, the antigenic domain being fused to
   B) an oligomerization domain (OMD), said oligomerization domain being fused via
   C) a linker domain to
   D) a peptidoglycan binding domain (PBD) consisting of a single copy of a LysM domain mediating the non-covalent attachment of the polypeptide to the BLP, and wherein the polypeptide as a whole contains only a single copy of a LysM domain; and
iii. a pharmaceutically acceptable diluent or excipient.

The concept of the invention thus relies on the unexpected finding that, for efficient and selective binding of oligomeric fusion proteins to a carrier particle, it is advantageous to use an oligomerization domain in combination with only a single copy of a binding domain which in nature is part of a repeated structure comprising multiple copies of the binding domain. For example, for binding to particles of other carrier entities, such as virosomes, liposomes or particles based on sugar polymers, having similar binding partners (e.g. derived from enzymes that degrade such particles), a fusion protein can be engineered comprising a non-repeating binding domain in an oligomer construct. Examples of other repeated binding domains from which a single copy can be used to bind to carrier entities in combination with an oligomerization domain include the following:

Choline binding domains from e.g. autolysins such the pneumococcal enzymeLytA (e.g. Pfam PF01473) for binding to carriers that contain choline.

Glucan binding domains from e.g. glycosyltransferases such as glucansucrases of oral streptococci (e.g. Pfam PF08363) for the binding to particles composed of glucose containing polymers.

Phosphatidylinositol lipid binding domains, e.g. the Pleckstrin homology (PH) domains (Pfam PF00169).

Antigenic Domain

The expression "surface exposed polypeptide or antigenic part thereof" is meant to refer to any stretch of amino acids which is found to be surface exposed in its natural context e.g. as part of a pathogen or on a tumour cell, and which is capable of mounting a protective immune response. Known or yet to be discovered antigenic sequences of pathogenic or tumour origin may be used in the present invention. The surface exposed pathogenic polypeptide is for example of viral, bacterial, or parasitic origin. In a preferred embodiment, it is a viral protein. For example, a surface exposed polypeptide of pathogenic origin comprises an ectodomain of an enveloped virus protein, or antigenic part thereof. Exemplary enveloped viruses include influenza virus, coronavirus, human respiratory coronaviruses, human immunodeficiency virus (HIV), metapneumovirus, paramyxovirus, in particular respiratory syncytial virus (RSV). In a specific aspect, the surface exposed polypeptide or antigenic part thereof is selected from the group consisting of influenza hemagglutinin ectodomain or part thereof, influenza neuraminidase ectodomain or part thereof, coronavirus spike (S) protein ectodomain or part thereof, RSV glycoprotein F ectodomain or part thereof, HIV gp140 or part thereof and RSV glycoprotein G ectodomain or part thereof.

Exemplary antigens from tumour cells include receptor tyrosine kinases (RTKs). RTKs are the high-affinity cell surface receptors for many polypeptide growth factors, cytokines, and hormones. Growth factor receptors include: epidermal growth factor receptor, fibroblast growth factor receptors and platelet-derived growth factor receptor. Hormone receptors include: androgen receptor and estrogen receptor. An example of the epidermal growth factor receptor (EGFR) is the ErbB protein family of four structurally related RTKs. The four members of the ErbB protein family are capable of forming homodimers, heterodimers, and possibly higher-order oligomers upon activation by a subset of potential growth factor ligands. ErbB-1 is overexpressed in many cancers. The platelet-derived growth factor receptor (PDGF) family consists of PDGF-A, -B, -C and -D, which form either homo- or heterodimers (PDGF-AA, -AB, -BB, -CC, -DD). The four PDGFs are inactive in their monomeric forms.

Peptidoglycan Binding Domain

A polypeptide of the invention is characterized by the presence of only a single copy of a LysM (Lysin motif) domain capable of mediating polypeptide binding to peptidoglycan. The LysM domain, also referred to in the art as "LysM repeat", is about 45 residues long. It is found in a variety of enzymes involved in bacterial cell wall degradation (Joris et al., FEMS Microbiol. Lett. 70 [1992], 257-264; Andre et al., J. Bacteriol. [2008], 7079-7086). The LysM domain is assumed to have a general peptidoglycan binding function. The structure of this domain is known (The structure of a LysM domain from *E. coli* membrane-bound lytic murein transglycosylase D (MltD). Bateman and Bycroft, J. Mol. Biol. 299 [2000], 1113-1119). The presence of the LysM domains is not limited to bacterial proteins. They are also present in a number of eukaryotic proteins, whereas they are lacking in archaeal proteins. A cell wall binding function has been postulated for a number of proteins containing LysM domains. Partially purified muramidase-2 of *Enterococcus hirae*, a protein similar to AcmA and containing six LysM domains, binds to peptidoglycan fragments of the same strain. The p60 protein of *Listeria monocytogenes* contains two LysM domains and was shown to be associated with the cell surface. The muropeptidases LytE and LytF of *Bacillus subtilis* have three and five repeats, respectively, in their N-termini and are both cell wall-bound.

It is important to note that previous studies, e.g. WO99/25836 in the name of the applicant and Bosma et al. (Appl. Environm. Microbiol. 72 [2006], 880-889) indicated that a single LysM domain is very poor in binding to BLPs and that increasing the number of LysM domains enhanced binding to BLPs. This is in line with the fact that most naturally occurring peptidoglycan binding proteins contain multiple (e.g. 2-6) tandem repeats of a LysM domain. In contrast, it was found in the present invention that binding of native oligomeric protein antigens to a particulate carrier is most efficient if only a single LysM domain is used in combination with an oligomerization domain (OMD), provided that a linker sequence is present between the OMD and the LysM domain.

A skilled person will be able to identify a LysM domain amino acid sequence (Buist et al., Mol. Microbiol. 68 [2008], 838-847; Visweswaran et al., Appl. Microbiol. Biotechnol. 92 [2011], 921-928) by conducting a homology-based search in publicly available protein sequence databases using methods known in the art. The PFAM website provides two profile hidden Markov models (profile HMMs) which can be used to do sensitive database searching using statistical descriptions of a sequence family's consensus. HMMER is a freely distributable implementation of profile HMM software for protein sequence analysis. As used herein, the term "LysM domain" typically refers to an amino acid sequence showing at least 50%, preferably at least 60%, most preferably at least 70% sequence similarity to the sequence according to PFAM accession number PF01476 for the LysM domain (see http://www.sanger.ac.uk/cgi-bin/Pfam/getacc?PF01476).

Numerous binding assays have been described in the art which allow the skilled person to determine whether a LysM domain has the required peptidoglycan binding capacity. As also described herein below, host cells can be transfected with the construct to be evaluated after which the host cells are allowed to express and secrete the recombinant polypeptide of interest in the culture supernatant. Secreted proteins are then assayed for selective binding to peptidoglycan particle obtained from a Gram-positive bacterium (bacterium-like particle or BLP) prepared by a well established acid treatment procedure. For example, 0.15 mg BLPs (dry weight) are contacted with an excess of cleared mammalian host cell expression culture supernatant and incubated for 30 minutes at room temperature while mixing gently. BLPs with bound protein are then collected by low-speed centrifugation. The pellet is analyzed for polypeptide bound to BLPs by SDS-PAGE and Western blotting using the appropriate antiserum. The amount of BLP-bound protein may be determined and quantified by SDS-PAGE and subsequent Coomassie blue staining using e.g. purified BSA as a reference protein.

As another example, fusions with (green) fluorescent protein can be prepared whose binding behaviour to the surface of *Lactococcus* can be assayed. See for instance Hu et al., Appl. Environ. Microbiol. 8 [2010], 2410-2418.

In one embodiment, a polypeptide of the invention contains only a single copy of a LysM domain found in the C-terminal region of the major autolysin AcmA of *L. lactis* which contains three homologous LysM domains separated by non-homologous sequences (Protan). The C-terminal region of AcmA was shown to mediate peptidoglycan binding of the autolysin (Buist et al., J. Bacteriol. 177 [1995], 1554-1563). For the amino acid sequences of the three AcmA LysM domains see for example FIG. 2 in WO99/25836 (wherein the three LysM domains are indicated by R1, R2 and R3), herein incorporated by reference.

Variations within the exact amino acid sequence of an AcmA LysM domain are also comprised, under the provision that the peptidoglycan binding functionality is maintained. Thus, amino acid substitutions, deletions and/or insertions may be performed without losing the peptidoglycan binding capacity. Some parts of the AcmA LysM domains are less suitably varied, for instance the conserved GDTL, N and GQ motifs found in most LysM domains. Others may however be altered without affecting the efficacy of the LysM domain to bind the carrier. For example, amino acid residues at positions which are of very different nature (polar, apolar, hydrophilic, hydrophobic) amongst the three LysM domains of AcmA can be modified. Preferably, the polypeptide of the invention comprises a sequence that is at least 70%, preferably 80%, more preferably 90%, like 92%, 95%, 97% or 99%, identical to one of the three LysM domains of *L. lactis* AcmA.

The 'percentage of amino acid sequence identity' for a polypeptide, such as 70, 80, 90, 95, 98, 99 or 100 percent sequence identity may be determined by comparing two optimally aligned sequences over a comparison window, wherein the portion of the polypeptide sequence in the comparison window may include additions or deletions (i.e. gaps) as compared to the reference sequence (which does not comprise additions or deletions) for optimal alignment of the two amino acid sequences. The percentage is calculated by: (a) determining the number of positions at which the identical amino acid occurs in both sequences to yield the number of matched positions; (b) dividing the number of matched positions by the total number of positions in the window of comparison; and (c) multiplying the result by 100 to yield the percentage of sequence identity. Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul et al., J. Mol. Biol. 215 [1990], 403; Altschul et al., Nucleic Acid Res. 25 [1997], 3389-3402) and ClustalW programs both available on the internet.

As another example, the LysM domain sequence from *Lactobacillus fermentum* Bacteriophage Endolysin (Hu et al., Appl. Environ. Microbiol., 76 [2010], 2410-2418) or a sequence showing at least 70% sequence identity thereto may also be used in the present invention.

Oligomerization Domain

As described above, a polypeptide of the invention is characterized by the presence of a oligomerization domain (OMD) and a single LysM domain. The OMD is for example a dimerization, trimerization or tetramerization domain. Such domains are known in the art (O'Shea et al., Science 243 [1989], 534-542; Harbury et al., Science 262 [1993], 1401-1407). For example, the oligomerization domain is a GCN4-based dimerization, trimerization or tetramerization domain. The leucine zipper region of the yeast transcriptional activator GCN4 comprises the GCN4-p1 dimerization domain with amino acid sequence MKQLEDKVEELLSKNYHLENEVARLKKLVGER (SEQ ID NO. 1). A GCN4-based trimerization domain (GCN4-pII) preferably comprises the amino acid sequence MKQIEDKIEEIESKQKKIENEIARIKK (SEQ ID NO. 2).

The term "tetramerization domain" as used herein is defined as a domain that mediates the formation of a tetramer out of four monomeric proteins or parts thereof. Suitable tetramerization domains include, but are not limited to, the Sendai virus phosphoprotein tetramerization domain and a tetramerization domain (GCN4-pLI) derived by mutation from the yeast GCN4 dimerization domain. In a preferred embodiment, tetramerization of a recombinant influenza neuraminidase ectodomain or part thereof is provided by a GCN4-based tetramerization domain. A GCN4-based tetramerization domain preferably comprises the amino acid sequence MKQIEDKLEEILSKLYHIENELARIKKLLGE (SEQ ID NO. 3).

Other useful oligomerization domains for use in the present invention include the C-terminal domain sequence of bacteriophage T4 fibritin (foldon) or functional part or analog thereof, in particular the C-terminal 27 to 30 residues of foldon (Gü the et al. J. Mol. Biol. 337 [2004], 905-915), and the soluble trimerization domain of chicken cartilage matrix (CART) protein. The C-terminal oligomerization domain of chicken cartilage matrix protein is a trimeric coiled coil comprised of three identical 43-residues (Selvarajah et al. AIDS Res. Hum. Retroviruses, 24 [2008], 301-314).

The oligomerization domain for use in the present invention may furthermore include a double cysteine motif in between the antigenic domain and the coiled-coil motif in order to further stabilize oligomeric proteins (Louis et al., J. Biol. Chem. 278 [2003], 20278-20286; Magro et al., Proc. Natl. Acad. Sci. USA 109 [2012], 3089-3094).

Linker Domain

The examples herein below illustrate the importance of a linker domain for optimal functioning of the OMD and/or the LysM domain. Accordingly, the OMD and LysM are preferably separated by a linker domain consisting of between 10 and 60, preferably 20-50, more preferably 25-40 amino acid residues. Direct fusion of the OMD to the LysM domain yielded unfavourable results. Very good results were obtained using a linker domain having a length of about 30 (e.g. 28-32) amino acids. See Example 2 for details.

In one aspect, the linker domain comprises a linker sequence which is found in between the LysM repeats in the C-terminus of *L. lactis* AcmA. For example, L1: GASSAGNTNSGGSTTTITNNNSGTNSSST (SEQ ID NO. 4) (29 amino acids); L2: GSASSTNSGGSNNSASTTPTTSVTPAKPTSQ (SEQ ID NO. 5) (31 amino acids); or L3: QSAAASNPSTGSGSTATNNSNSTSSNSNAS (SEQ ID NO. 6) (30 amino acids). In a preferred embodiment, the linker domain consists of GAS SAGNTNSGGSTTTITNNNSGTNSSST (SEQ ID NO. 4), GSASSTNSGGSNNSASTTPTTSVTPAKPTSQ (SEQ ID NO. 5), or QSAAASNPSTGSGSTATNNSNSTSSNSNAS (SEQ ID NO. 6). Other linker domain sequences of a correct length (i.e. between about 10 and 60 amino acid residues) may also be used. The skilled person will be able to produce and assess the suitability of a given linker sequence based on the Examples shown below and his general knowledge.

It was furthermore found that the production of a polypeptide of the invention can be enhanced by the presence of a terminal "capping domain". For example, expression of a construct consisting of, from N- to C-terminus, HA fused via an OMD and a linker sequence to a single LysM domain was increased upon the addition of a C-terminal capping domain (see FIG. 2A). Hence, a polypeptide of the invention may furthermore comprise in case of an N-terminal antigenic domain a C-terminal capping domain, or in case of a C-terminal antigenic domain an N-terminal capping domain. The capping domain may vary in length e.g. from about 10 to about 60 amino acids, preferably 20-50, more preferably 25-40 amino acid residues, in length. Very good results were obtained with a capping domain having a sequence identical to the linker domain connecting the OMD to the LysM domain. In other words, the single copy LysM domain in a polypeptide of the invention is advantageously flanked by identical or at least highly (>90%) similar amino acid sequences. Accordingly, in a specific embodiment the capping domain, and preferably also the linker domain, consists of an amino acid sequence selected from the group consisting of:

```
                                          (SEQ ID NO. 4)
    GASSAGNTNSGGSTTTITNNNSGTNSSST, (SEQ ID NO. 5)
    GSASSTNSGGSNNSASTTPTTSVTPAKPTSQ
    and (SEQ ID NO. 6)
    QSAAASNPSTGSGSTATNNSNSTSSNSNAS.
```

The relative orientation of the various domains within the polypeptide can vary, provided that a linker domain sequence is always located between the OMD and LysM domain. Suitable linker domains are described herein above.

In one embodiment, the LysM domain is located C-terminally from the polypeptide of pathogenic origin or antigenic part thereof. For instance, this configuration is particularly suitable for substances comprising type 1 membrane proteins such as influenza virus HA, HIV gp140, coronavirus S en RSV F. In another embodiment, the LysM domain is located N-terminally from the polypeptide of pathogenic origin or antigenic part thereof. The latter orientation is preferred for type 2 membrane proteins like influenza virus NA and RSV G. The polypeptide may furthermore contain one or more sequences facilitating recombinant expression in and/or secretion by a eukaryotic host cell. Advantageous sequences include N-terminal signal sequences. A "signal sequence" is herein defined as a signal peptide that directs transport of a protein or part thereof to the endoplasmic reticulum of a eukaryotic cell—the entry site of the secretory pathway. A signal sequence can be located N-terminal of the protein or part thereof. Signal peptides can be cleaved off after insertion of the protein into the endoplasmic reticulum. For example, in one embodiment a pMT/BiP vector for expression of recombinant protein in *Drosophila* cells comprises a BiP signal sequence. In another embodiment, a pCD5 vector for expression of recombinant protein in mammalian cells comprises the signal sequence MPMGSLQPLATLYLLGMLVA (SEQ ID NO. 7), for instance the signal peptide sequence of CD5 glycoprotein. In yet another embodiment, the signal sequence naturally preceding the protein is used to direct the precursor polypeptide to the secretory pathway.

As described herein above, a recombinant polypeptide of the invention produced is suitably used for the manufacture of an immunogenic composition in particulate form. A further aspect of the invention therefore relates to an immunogenic composition in particulate form, comprising as particulate carrier a non-viable spherical peptidoglycan particle obtained from a Gram-positive bacterium (GEM particle or bacterium-like particle (BLP)), wherein oligomers of recombinantly produced polypeptides are attached non-covalently to said BLP, each polypeptide being defined as herein above, and a pharmaceutically acceptable diluent or excipient.

BLPs are non-living, deprived of intact surface proteins and intracellular content which can be obtained by treating intact cells with a solution capable of removing cell-wall components such as a protein, (lipo)teichoic acid or carbohydrate from said cell-wall material without mechanical disruption and wherein the thick peptidoglycan cell wall remains intact. The resulting essentially spherical peptidoglycan microparticles reflect the size and shape of the Gram-positive bacterium. Preferably, the bacterium is a non-pathogenic bacterium, more preferably a food-grade bacterium. The bacterium can be selected from the group consisting of a *Lactococcus*, a *Lactobacillus*, a *Bacillus* and a *Mycobacterium* ssp.

Various embodiments are envisaged, for example the particulate carrier can be provided non-covalently with at least a first oligomer of polypeptides comprising surface exposed polypeptides or antigenic parts thereof derived from a first pathogen and with a second oligomer of polypeptides comprising distinct surface exposed polypeptides or antigenic parts thereof derived, e.g. from the same or from a second, distinct pathogen. The distinct oligomers for instance comprise different HA serotypes, HA and NA, HA and S and/or RSV F. The RSV F protein or an immunogenic active fragment thereof having at least 10 amino acid residues is the preferred one in terms of mediating protective antibody responses against RSV. The F protein remains highly conserved across both major strains of RSV (subgroup A and subgroup B). The F protein is synthesized as a non-fusogenic 67 kDa precursor (F0) that undergoes proteolytic cleavage by furin to produce two disulfide-linked polypeptides, F1 and F2. The F protein enters the cell membrane via the N-terminus of the F 1 polypeptide, whereas the transmembrane segment is located close to the C-terminus. Adjacent to these two regions are two heptad repeat sequences, denoted HR-C and HR-N, that form a stable trimer of hairpin-like structures that undergo a conformational change to enable the viral and cell membranes to be apposed before viral entry. In a preferred embodiment the F ectodomain contains two mutated cleavage sites resulting in a non-cleaved polypeptide locked in a prefusion conformation.

In a preferred embodiment, there is provided an immunogenic composition in particulate form, comprising oligomers of a surface exposed polypeptide of influenza virus origin, or antigenic part thereof, said oligomers being bound non-covalently to a particulate carrier, and a pharmaceutically acceptable diluent or excipient. An immunogenic composition according to the invention for instance comprises one recombinant trimeric influenza hemagglutinin ectodomain or part thereof or one recombinant tetrameric influenza neuraminidase ectodomain or part thereof. Such immunogenic composition is particularly suitable for eliciting an immune response in an individual against an influenza virus subtype or strain, or more than one related influenza virus subtypes or strains. In some embodiments however, an immunogenic composition according to the invention comprises a combination of one or more trimeric hemagglutinin ectodomains or parts thereof, and/or one or more tetrameric neuraminidase ectodomains or parts thereof.

Thus for example, 2, 3, 4, 5, 6, 7, 8, 9 or 10 trimeric hemagglutinin ectodomains or parts thereof can be combined, such as H1, H2, H3, H4, H5, H6, H7, H8, H9, H10, H11, H12, H13, H14, H15 and/or H16, or 2, 3, 4, 5, 6, 7, 8 or 9 tetrameric neuraminidase ectodomains or parts thereof can be combined, such as N1, N2, N3, N4, N5, N6, N7, N8 and/or N9. Additionally, an immunogenic composition according to the invention may comprise a combination of one or more trimeric hemagglutinin ectodomains or parts thereof and one or more tetrameric neuraminidase ectodomains or parts thereof of different influenza subtypes. For example, 1, 2, 3, 4, 5, 6, 7, 8, 9 or 10 trimeric hemagglutinin ectodomains or parts thereof and 1, 2, 3, 4, 5, 6, 7, 8 or 9 tetrameric neuraminidase ectodomains or parts thereof can be combined, such as H1, H2, H3, H4, H5, H6, H7, H8, H9, H10, H11, H12, H13, H14, H15, H16, N1, N2, N3, N4, N5, N6, N7, N8 and/or N9. It will be clear to a skilled person that the term "one or more ectodomains" encompasses one or more ectodomains from one or more influenza virus subtypes, such as for example Influenza A virus and Influenza B virus. Thus, an immunogenic composition in particulate form according to the invention can be a multivalent composition with which an improved protection against an influenza virus infection can be achieved as compared to an immunogenic composition comprising one recombinant trimeric influenza hemagglutinin ectodomain or part thereof or one recombinant tetrameric influenza neuraminidase ectodomain or part thereof. Additionally, or alternatively, with a multivalent composition a wider protection against more than one influenza virus type, or influenza virus subtypes or strains can be achieved. Furthermore, an immunogenic composition according to the invention may be less sensitive to antigenic alterations than traditional inactivated or live attenuated influenza virus vaccines.

A further embodiment of the invention relates to a method for providing an immunogenic composition in particulate form, comprising the steps of: (a) providing a recombinant polypeptide according to the invention; (b) providing a non-viable spherical peptidoglycan particle obtained from a Gram-positive bacterium (BLP); (c) allowing for non-covalent binding of said polypeptide to said BLP to form an immunogenic complex comprising oligomers of a polypeptide comprising a surface exposed polypeptide of pathogenic or tumour origin or antigenic part thereof bound non-covalently to a particulate carrier, and (d) formulating the immunogenic complex into an immunogenic composition.

As to step (b), means and methods for providing peptidoglycan microparticles (BLPs) are described in the art. See for example WO 02/101026 and U.S. Pat. No. 6,896,887 disclosing a method for obtaining cell-wall material of a Gram-positive bacterium comprising treating said cell-wall material with a solution capable of removing a cell-wall component such as a protein, (lipo)teichoic acid or carbohydrate from said cell-wall material wherein said cell-wall material essentially comprises spherical peptidoglycan microparticles. The particles thus obtained can simply be mixed with a preparation (e.g. a cell culture supernatant or purified polypeptide) comprising recombinantly produced polypeptide(s). By virtue of their LysM domain and OMD, the polypeptides can bind to a carrier, the binding being accompanied, preceded and/or followed by assembly into their native oligomeric configuration.

Also provided is a nucleic acid sequence encoding a polypeptide according to the invention, as well as a vector comprising the nucleic acid sequence. The term "vector" as used herein is defined as a nucleic acid molecule, such as a plasmid, bacteriophage or animal virus, capable of introducing a heterologous nucleic acid sequence into a host cell. A vector according to the invention allows the expression or production of a protein or part thereof encoded by the heterologous nucleic acid sequence in a host cell. Vectors suitable in a method according to the invention include, but are not limited to, pCD5 (Pouyani and Seed, Cell 83 [1995], 333-343) and pCAGGS (Niwa et al., Gene 108 [1991], 193-199). A "host cell" is a cell which has been transformed, or is capable of transformation, by a nucleic acid molecule such as a vector. The term "transformation" is herein defined as the introduction of a foreign nucleic acid into a recipient cell. Transformation of a recipient cell can result in transient expression of a recombinant protein by said cell, meaning that the recombinant protein is only expressed for a defined period of time. Alternatively, transformation of a recipient cell can result in stable expression, meaning that the nucleic acid is introduced into the genome of the cell and thus passed on to next generations of cells. Additionally, inducible expression of a recombinant protein can be achieved. An inducible expression system requires the presence or absence of a molecule that allows for expression of a nucleic acid sequence of interest. Examples of inducible expression systems include, but are not limited to, Tet-On and Tet-Off expression systems, hormone inducible gene expression systems such as for instance an ecdysone inducible gene expression system, an arabinose-inducible gene expression system, and a Drosophila inducible expression system using a pMT/BiP vector (Invitrogen) which comprises an inducible metallothioneine promoter.

A still further embodiment relates to a host cell comprising a nucleic acid sequence or a vector according to the invention. Such a host cell is advantageously used for the recombinant production of a polypeptide disclosed herein.

A recombinant polypeptide of the invention is for instance expressed in a prokaryotic cell, or in a eukaryotic cell, such as a plant cell, a yeast cell, a mammalian cell or an insect cell. Additionally a recombinant oligomeric ectodomain or part thereof according to the invention can be expressed in plants. Prokaryotic and eukaryotic cells are well known in the art. A prokaryotic cell is for instance E. coli or L. lactis. Examples of plants and/or plant cells include, but are not limited to, corn (cells), rice (cells), duckweed (cells), tobacco (cells, such as BY-2 or NT-1 cells), and potato (cells). Examples of yeast cells are Saccharomyces and Pichia. Examples of insect cells include, but are not limited to, Spodoptera frugiperda cells, such as Tn5, SF-9 and SF-21 cells, and Drosophila cells, such as Drosophila Schneider 2 (S2) cells. Examples of mammalian cells that are suitable for expressing a recombinant protein according to the invention include, but are not limited to, African Green Monkey kidney (Vero) cells, baby hamster kidney (such as BHK-21) cells, Human retina cells (for example PerC6 cells), human embryonic kidney cells (such as HEK293 cells), Madin Darby Canine kidney (MDCK) cells, Chicken embryo fibroblasts (CEF), Chicken embryo kidney cells (CEK cells), blastoderm-derived embryonic stem cells (e.g. EB14), mouse embryonic fibroblasts (such as 3T3 cells), Chinese hamster ovary (CHO) cells, and mouse myelomas (such as NS0 and SP2/0), and derivatives of these cell types. In a preferred embodiment mammalian CHO cells or S2 insect cells are used.

Herewith, the invention also provides a method for providing a recombinant polypeptide according to the invention, comprising culturing a host cell described above in a suitable medium, allowing for expression of the polypeptide and isolating the substance. Preferably, the method uses a eukaryotic host cell, preferably a mammalian host cell, for example an MDCK, HEK, CHO or PerC6 cell, or an insect cell, for example an S2 cell.

Further provided by the invention is a method for eliciting an immune response against a pathogen in a mammalian individual comprising administering to said individual an immunogenic composition according to the invention.

The invention provides immunogenic compositions which may be used as vaccines. These vaccines may either be prophylactic (i.e. to prevent infection) or therapeutic (i.e. to treat infection), but will typically be prophylactic. The invention also provides a method for raising an immune response in a mammal comprising the step of administering an effective amount of an immunogenic composition of the invention. The immune response is preferably protective and preferably involves antibodies and/or cell-mediated immunity. The method may raise a booster response. The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. >50 years old, >60 years old, and preferably >65 years). The vaccines are not suitable solely for these age groups, however, and may be used more generally in a population, including for the young (e.g. <5 years old), hospitalised patients, healthcare workers, armed service and military personnel, pregnant women, the chronically ill, or immunodeficient patients.

For example, the invention provides a method for eliciting an immune response against a viral disease in an individual, preferably wherein the viral disease is caused by influenza virus, animal coronavirus, human respiratory coronaviruses, human immunodeficiency virus (HIV), or paramyxovirus, in particular respiratory syncytial virus (RSV) or metapneumovirus. The method involves administering to said individual a native oligomeric subunit vaccine of the invention comprising a:

A) an N- or C-terminal antigenic domain, comprising at least one surface exposed polypeptide of pathogenic origin or antigenic part thereof, selected from the group consisting of influenza hemagglutinin (HA) ectodomain or part thereof, influenza neuraminidase (NA) ectodomain or part thereof, coronavirus spike (S) protein ectodomain or part thereof, RSV glycoprotein F or G ectodomains or parts thereof and HIV gp140 ectodomain or part thereof, the antigenic domain being fused to B) an oligomerization domain (OMD), said oligomerization domain being fused via C) a linker domain to D) a peptidoglycan binding domain (PBD) consisting of a single copy of a LysM domain capable of mediating the non-covalent attachment of the polypeptide to a non-viable bacterium-like particle (BLP) obtained from a Gram-positive bacterium, and wherein the polypeptide as a whole contains only a single copy of a LysM domain.

The composition according to the invention can be administered by any way known by the man skilled in the art, with preferences for nasal, sublingual, oral or parenteral administration routes. In a preferred embodiment, the route of administration is the nasal route. The invention also provides a delivery device pre-filled with an immunogenic composition of the invention. Suitable delivery devices include pre-filled (spray) containers and syringes. Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, sublingual, oral (e.g. tablet, spray), vaginal, topical, transdermal or transcutaneous, intranasal, ocular, aural, pulmonary or other mucosal administration. Intramuscular administration is typical, as discussed above.

The invention may be used to elicit systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). Immunogenic compositions of the invention can be administered to the same patient every year, every 2 years, every 3 years, etc.

Also envisaged is co-administration of different respiratory vaccines to a subject at the same time e.g. to administer a pneumococcal vaccine at the same time as an influenza vaccine. Combination vaccines, in which two or more vaccines are administered as a mixture, like combined pneumococcal saccharides (conjugated or unconjugated) with a respiratory syncytial virus (RSV) antigen, and is also speculated that a number of other antigens such as an influenza virus antigen might be added. For example, the present invention may be applied for the manufacture of a combination vaccine comprising a combination of the fusion (F), attachment (G) and matrix (M) proteins of RSV with an influenza vaccine.

The invention also relates to the use of a vaccine composition or of a method for the preparation of a vaccine composition, as above described, for immunizing mammal against natural conformational antigen, particularly against influenza or RSV infections, or to produce antibodies directed against conformational antigen, such as HA, NA or RSV antigen. In one aspect, the invention provides the use of a recombinant polypeptide according to the invention for the preparation of a vaccine or immunogenic composition intended to prevent or to treat influenza or RSV infection.

LEGENDS TO THE FIGURES

FIG. 1. Schematic representation (panels A and B) and binding to BLPs (panels C and D), and multimerization state (E) of various HA fusion proteins. Schematic representation of linear HA-OMD-Protan (panel A) that is able to form trimers (abbreviated as HA-P$^{tri}$) and HA-Protan (panel B) that exists as a monomer (abbreviated as HA-P$^{mon}$). The OMD is the GCN4-pII. The Protan part (=PBD) of the fusion varies in size. The number following the letter P in the abbreviated protein fusion name indicates the number of LysM domains in the Protan part. L1-2: linker sequences. The L following the number in the abbreviated protein fusion name indicates the presence of a C-terminal linker domain after the most C-terminal LysM domain. LysM1-2: LysM (peptidoglycan binding) domains.

Panels C and D show that only 1 LysM domain is required for efficient binding to BLPs when the HA-Protan fusion proteins contain a GCN4 domain (OMD). Three different HA-Protan fusion protein variants without GCN4 trimerization motif and one such fusion protein containing a GCN4 motif were expressed in HEK293S (GNTI-) cells. This was done for HA proteins originating from H1M (panel C) and from X31 (panel D) in duplicate. The HA-Protan fusion proteins obtained were allowed to bind to BLPs by incubating 150 μg (dry weight) of the particles with an excess amount of approximately 30-45 μg of the fusion proteins after which the particles were collected. Then 50 μg of each BLP-fraction was analyzed by SDS-PAGE and Coomassie Blue staining [panels I]. As a control expression was checked by analyzing samples from the cell culture media by SDS-PAGE and Western blotting [panels II] using MAb PA90 (α-Protan). All fusion proteins were well expressed. Together, these experiments show that a single LysM domain combined with an OMD is sufficient for efficient binding of proteins to BLPs whereas two LysM domains are required for efficient binding when no OMD is present. Panel E: OMD-containing HA-Protan fusion proteins are predominantly oligomeric. Analyses of different HA-GCN4-Protan variants by blue native gel electrophoresis followed by Western blot using the Protan antibody α-PA90. Of each variant, equal amounts of the cleared cell culture supernatant were boiled for 10 seconds (10"), 30 seconds (30") or 3 minutes (3') before application to the gel. HA-Protan fusion proteins analyzed were the H1M virus derived HA-P1$^{tri}$ and HA-P1L$^{tri}$ proteins. All these HA proteins migrated with the mobility corresponding to that of a trimer after very brief heating (10 sec), but dissociated into dimeric and monomeric forms of HA after longer boiling times. HA-P1$^{tri}$ and HA-P1L$^{tri}$ trimers remained detectable even after prolonged boiling of the samples. All the equivalent HA-P$^{mon}$ variants migrated with the mobility of a monomer. In addition, most of these HA-P$^{mon}$ proteins exhibited a variable, but sometimes strong tendency to form high molecular weight aggregates (indicated by the asterisks), most likely as a result of the poor folding and stability of these non-native proteins.

FIG. 2. Schematic presentation of HA-P2L$^{tri}$ and HA-P1L$^{tri}$ variants and the binding thereof to BLPs for the production of vaccines. Panel A: production of HA-P2L$^{tri}$ and HA-P1L$^{tri}$ results mainly in trimeric variants but also low amounts of unwanted, not properly folded, monomeric variants are produced. Panel B: binding of mono- and trimeric HA-P2L$^{tri}$ variants to BLPs followed by subsequent washing results in BLP vaccines with bound native oligomeric HA and the unwanted not properly folded monomeric HA. Binding of mono- and trimeric HA-P1L$^{tri}$ variants to BLPs followed by subsequent washing results in BLP vaccines with bound native oligomeric HA and without the unwanted not properly folded monomeric HA. Therefore, binding of proteins to BLPs using a single LysM domain combined with an OMD such as GCN4 allows for selective binding of the desired native biological active oligomeric proteins.

Figure 3:
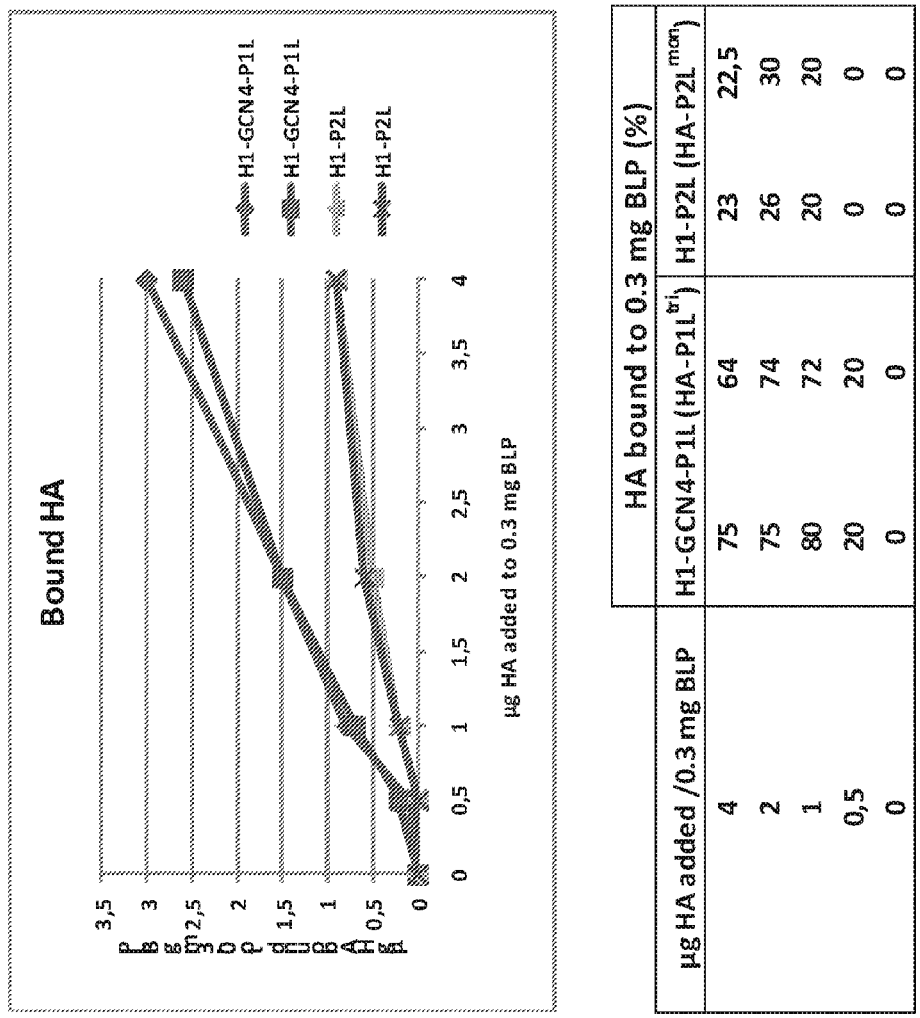

FIG. 3. Amount of bound HA-Protan variants with and without OMD to BLPs. Increasing amounts (0-4 μg) of HA-P1L$^{tri}$ (H1-GCN4-P1L) and HA-P2L$^{mon}$ (H1-P2L) were allowed to bind to a fixed amount (0.3 mg) BLPs. After binding the amount of bound HA was determined. The experiment was performed in duplicate. Clearly, more HA-P1L$^{tri}$ binds to BLPs at similar concentrations as used for HA-P2L$^{mon}$. Hence, binding of proteins to BLPs using a single LysM domain combined with an OMD such as GCN4 is more efficient than with two LysM domains without an OMD.

Figure 4:
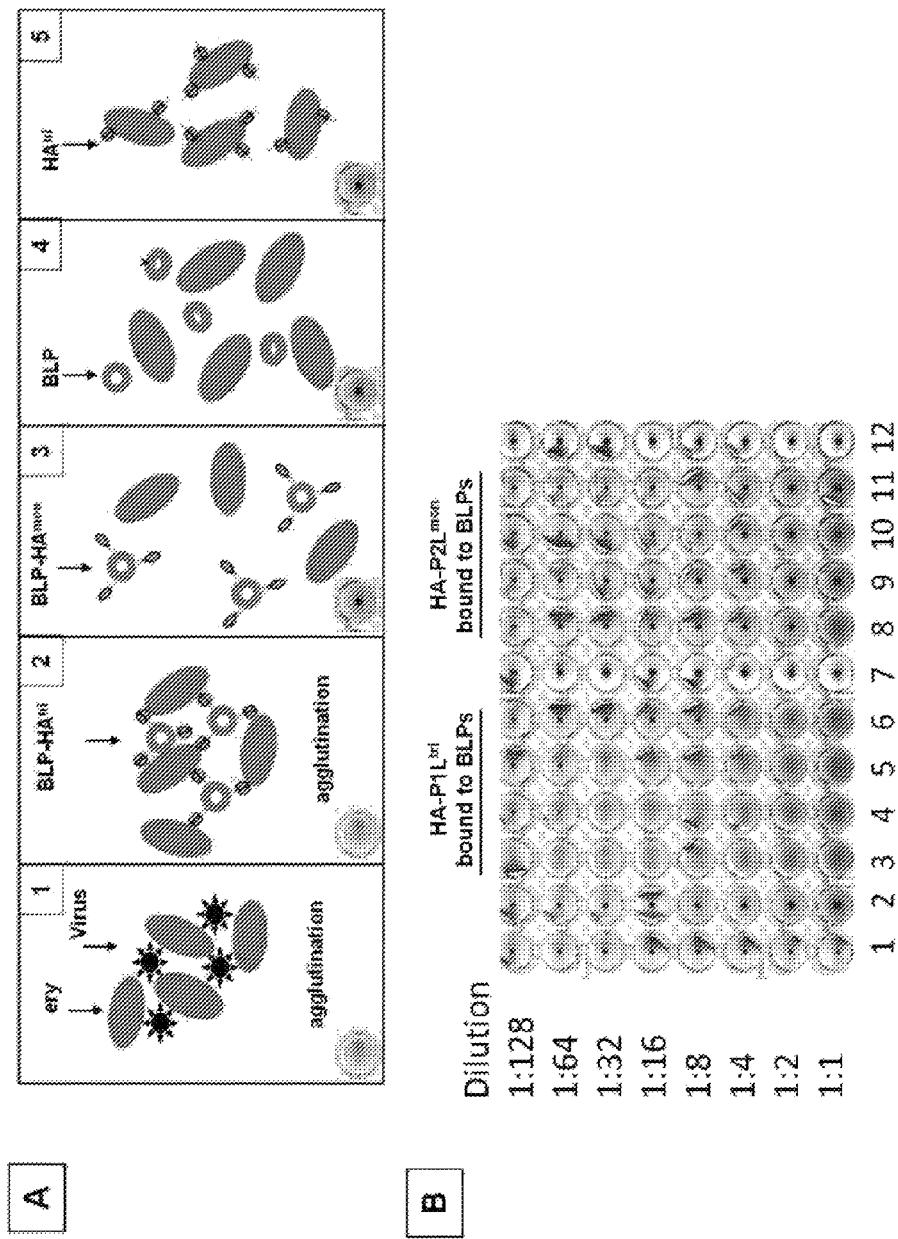

FIG. 4. Oligomeric HA (in contrast to monomeric HA) bound to BLPs is biologically functional in an agglutination test. A. Schematic representation of the haemagglutination assay. Panel 1: influenza virus mixed with red blood cells (RBCs; ery) are able to bind to RBCs and are able to form networks that cause agglutination. Panel 2: HA trimers attached to BLPs (BLP-HA$^{tri}$) and mixed with RBCs are able to bind to RBCs, and are able to form networks that cause agglutination. Panel 3: HA monomers attached to BLPs (BLP-HA$^{mon}$) and mixed with RBCs are not able to bind to RBCs, and are not able to form networks that cause agglutination; the RBCs sediment in wells of a microtiter plate, which is visible as a dot. Panel 4: BLPs mixed with RBCs are not able to bind to RBCs and do not cause agglutination. Panel 5: HA trimers (HA$^{tri}$) bind to RBCs, but are not able to form in networks that cause agglutination.

B. Haemagglutination assay using turkey RBCs. The HA used in the fusions is H1M. Lane 1: negative control, RBCs+buffer. Lane 2: RBCs+BLP. Lane 3: RBCs+BLP with 4 µg bound HA-P1L$^{tri}$. Lane 4: RBCs+BLP with 2 µg bound HA-P1L$^{tri}$. Lane 5: RBCs+BLP with 1 µg bound HA-P1L$^{tri}$. Lane 6: RBCs+BLP with 0.5 µg bound HA-P1L$^{tri}$. Lane 7: RBCs+4 µg HA-P1L$^{tri}$. Lane 8: RBCs+BLP with 4 µg bound HA-P2L$^{mon}$. Lane 9: RBCs+BLP with 2 µg bound HA-P2L$^{mon}$. Lane 10: RBCs+BLP with 1 µg bound HA-P2L$^{mon}$. Lane 11: RBCs+BLP with 0.5 µg bound HA-P2L$^{mon}$. Lane 12: RBCs+4 µg HA-P2L$^{mon}$. This experiment clearly shows that only oligomeric HA bound to BLPs (BLP-HA$^{tri}$) is biologically functional, whereas monomeric HA bound to BLPs (BLP-HA$^{tri}$) is not.

Figure 5:
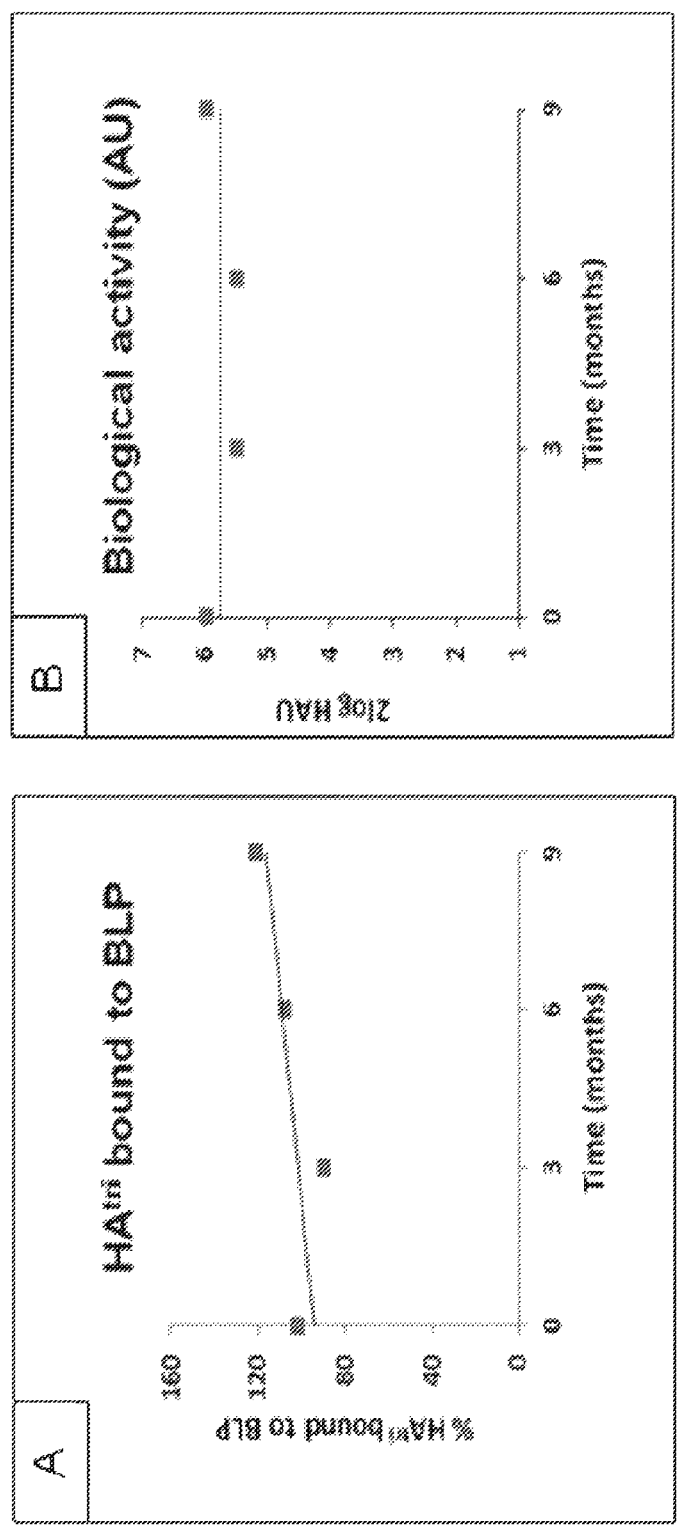

FIG. 5. Stability of HA-P1L$^{tri}$ bound to BLPs. Panel A: HA-P1L$^{tri}$ bound to BLPs (ratio 3.3 µg HA-P1L$^{tri}$ bound to 1 mg BLPs) was aliquoted and stored at 2-8° C. At T=0, 3, 6 and 9 months post formulation an aliquot was tested for the amount of HA-P1L$^{tri}$ bound to BLPs (amount measured at T=0 set at 100%); and panel B: biological activity in an agglutination test. AU; agglutination units. This experiment clearly shows that HA-P1L$^{tri}$ bound to BLPs is completely stable and biological functional up to at least 9 months of storage in PBS at 2-8° C.

Figure 6:
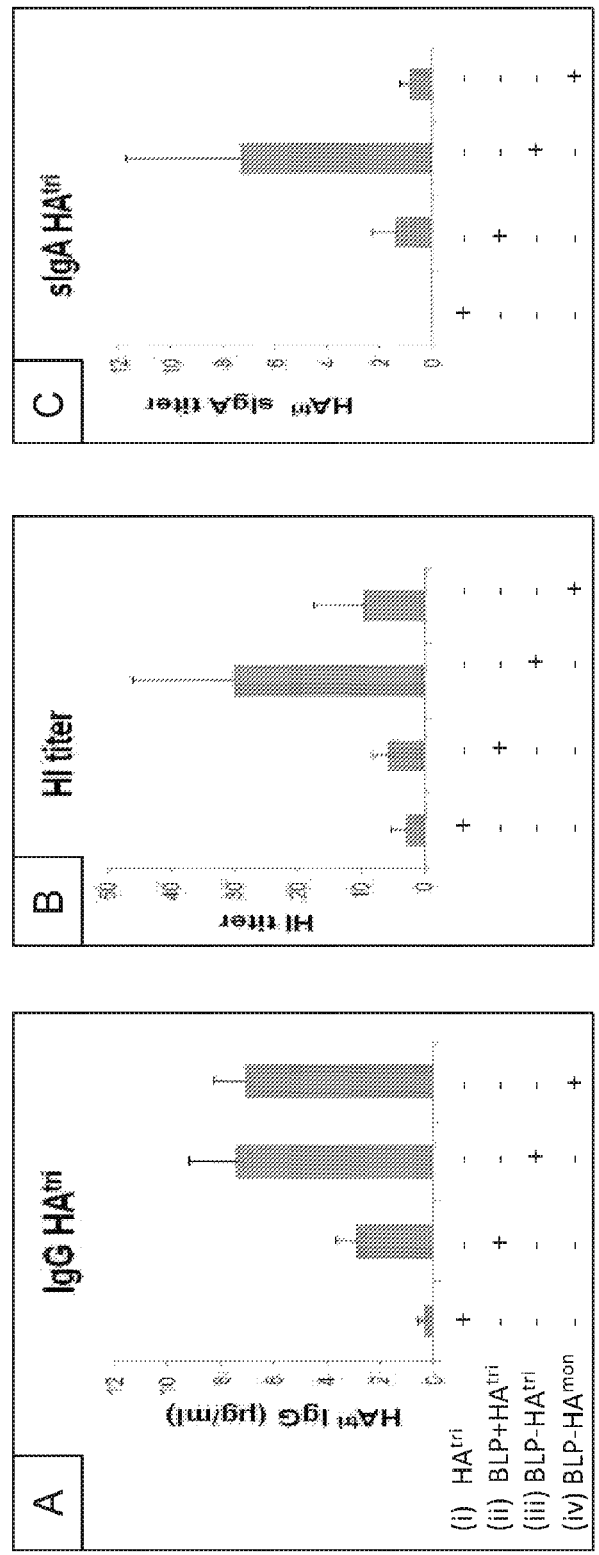

FIG. 6. Average amount of anti-H1M IgG antibodies in µg/ml (panel A); HI titers (panel B) present in the serum; and S-IgA (panel C) present in nose wash of mice immunized three times intranasally with: (i) soluble trimeric HA (HA$^{tri}$) [0.33 µg per dose]; (ii) soluble trimeric HA mixed with BLP (BLP+HA$^{tri}$) [0.33 µg HA$^{tri}$ and 0.1 mg BLP per dose]; (iii) trimeric HA (HA-P1L$^{tri}$) bound to BLPs (BLP-HA$^{tri}$) [0.33 µg HA$^{tri}$ and 0.1 mg BLP per dose], and (iv) monomeric HA (HA-P1L$^{mon}$) bound to BLPs (BLP-HA$^{mon}$) [0.33 µg HA$^{tri}$ and 0.1 mg BLP per dose]. Clearly, the BLP-HA$^{tri}$ particulate formulation was the most immunogenic formulation as compared to soluble trimeric HA (HA$^{tri}$) and soluble trimeric HA mixed with BLP (BLP+HA$^{tri}$). With respect to functional antibody assays (HI titers; panel B and S-IgA; panel C) the oligomeric BLP-HA$^{tri}$ particulate formulation elicited higher responses than the monomeric BLP-HA$^{mon}$ particulate formulation showing that biologically functional HA$^{tri}$ is the most immunogenic conformation.

Figure 7:
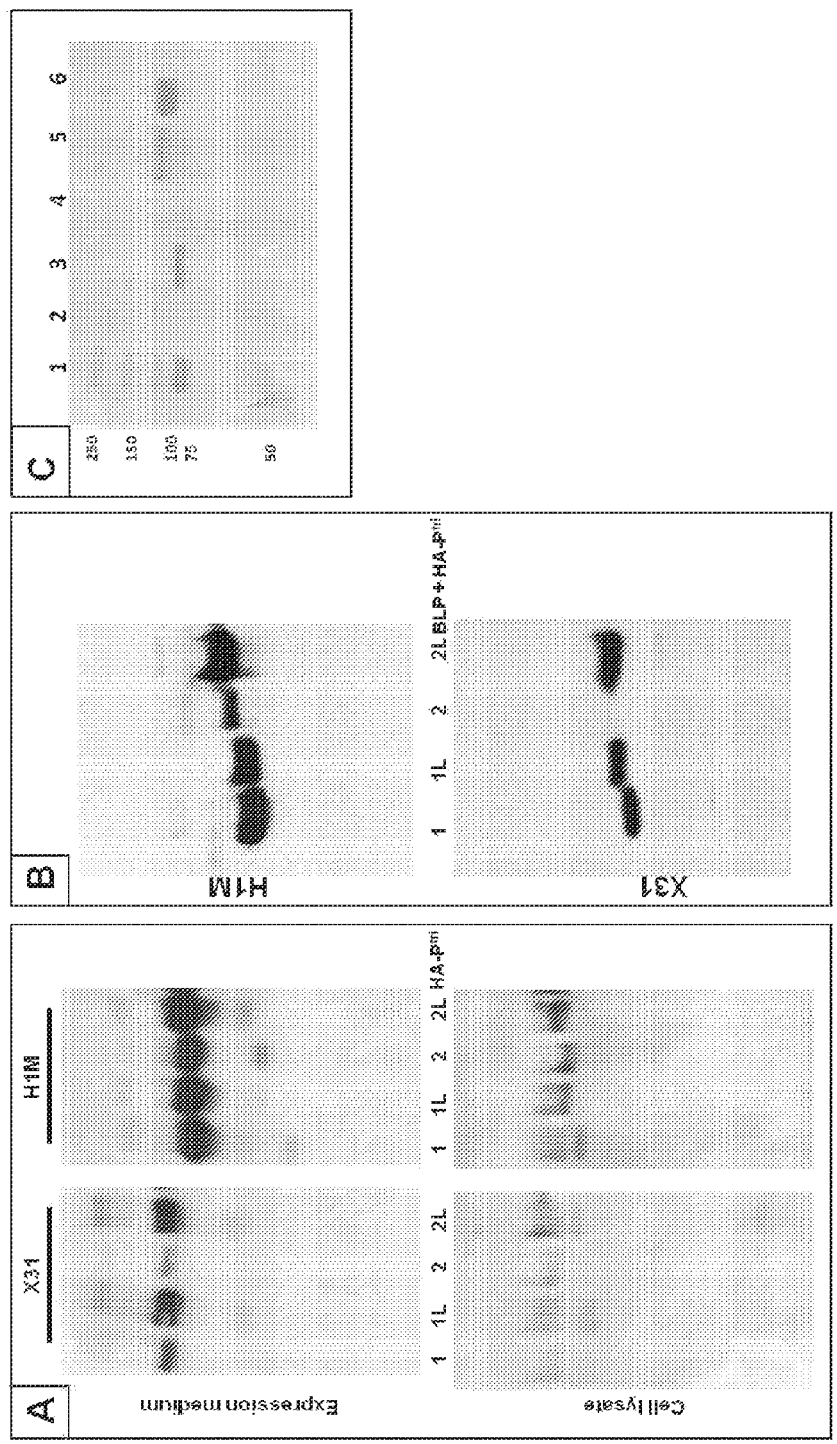

FIG. 7. Expression and BLP binding characteristics of HA$^{tri}$-Protan, GCN4 (OMD) containing fusion proteins with various Protan moieties. Panel A: HEK 293 cells were transfected with the respective expression plasmids and incubated after which culture supernatants were harvested and cells lysed. Samples of each were analyzed by SDS-PAGE and Western blotting, using an antibody directed against the Protan moiety (α-PA90). The production of a series of GCN4-containing HA proteins (designated HA-P$^{tri}$ to indicate their trimerization potential) of subtypes H3 (X31) and H1 (H1M) are shown. All HA-P$^{tri}$ variants were readily expressed and efficiently secreted into the cell culture medium as judged from their limited presence in the cell lysates. The X31 HA-P$^{tri}$ fusion proteins were produced somewhat less abundant than the H1M HA-P$^{tri}$ fusion proteins, while in general the HA proteins fused to P1L and P2L seemed to display the highest production levels with the most limited retention in the cells. Panel B: different GCN4 containing HA-Protan fusion proteins were compared for their binding to BLPs by incubating equal amounts of the particles in the presence of excess amounts of fusion proteins and analyzing the amounts of the BLP-bound proteins by SDS-PAGE and Western blotting. All HA-P$^{tri}$ variants were found to bind but with markedly varying efficiencies. Both for the H1M and the X31 virus derived HA proteins, variants HA-P1$^{tri}$, HA-P1L$^{tri}$ and HA-P2L$^{tri}$ bound to the BLPs most efficiently. Low binding efficiency was observed for the H1M1 and X31 HA-P2$^{tri}$ proteins to BLPs. This result indicates that 1 LysM domain in combination with an OMD is sufficient to enable excellent binding to BLPs. Panel C: Western blot incubated with anti-HA (anti-H1M). Lane 1: marker proteins, sizes indicated in the margin in kDa. Lane 2: BLP particles, 30 µg. Lane 3: HA$^{tri}$, which carries a Strep tag (HA-Strep$^{tri}$) instead of a Protan extension (40 ng). Lane 4: BLPs (30 µg) recovered from an incubation with HA-Strep$^{tri}$ (840 ng). Lane 5: HA-P1L$^{tri}$, 44 ng. Lane 6: BLPs (30 µg) recovered from an incubation with HA-P1L$^{tri}$ (880 ng). Altogether these experiments show that the fusion proteins are well expressed and secreted from the mammalian cells and that the presence of the bacterial Protan domain at the C-terminus did not interfere with efficient secretion of the HA-oligomeric fusion proteins (panel A). Moreover, this experiment clearly shows that 1 LysM domain is sufficient to obtain excellent binding to BLPs and that the GCN4 domain, while required to enhance the binding of a single LysM domain, does not bind to BLPs (panel C).

Figure 8:
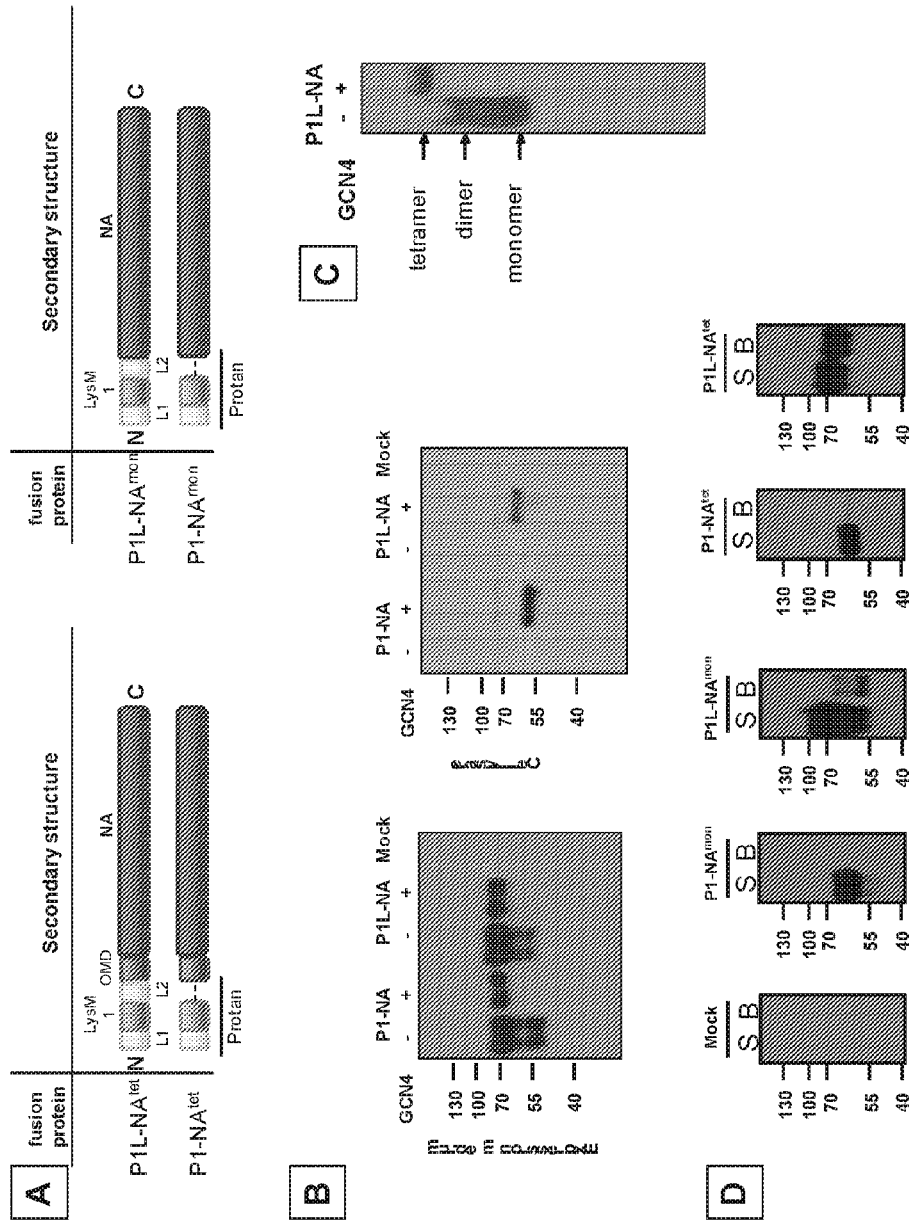

FIG. 8. Schematic representation (A), expression (B), multimerization state (C) and binding to BLPs (D) of Protan-NA. Panel A: Schematic representation of linear Protan-OMD-NA that is able to form tetramers (abbreviated as P-NA$^{tet}$) and Protan-NA that exists as a monomer (abbreviated as P-NA$^{mon}$) fusions. The OMD is the GCN4-pLI in the NA constructs. The Protan part (=PBD) of the fusion contains 1 LysM domain with or without linker. The L following the number in the abbreviated protein fusion name indicates the presence of a C-terminal linker domain after the LysM domain. Panel B: shows the expression of Protan-NA fusion proteins with or without GCN4 tetramerization motif. HEK 293 cells were transfected with the respective expression plasmids and incubated after which culture supernatants were harvested and cells lysed. Samples of each were analyzed by SDS-PAGE and Western blotting, using an antibody directed against the Protan moiety (α-PA90). Similar to the HA-Protan proteins, all Protan-NA variants were found to be secreted into the cell culture supernatant; minor intracellular retention was observed for the Protan-NA variants containing the GCN4 tetramerization motif. Panel C: shows that OMD-containing NA-Protan fusion proteins are oligomeric. Here the oligomeric state of P1L-NA variants with (+) and without (−) GCN4 was compared. Samples of these P1L-NA variants were analysed by blue-native gel electrophoresis. Most of the P1L-NA$^{mon}$ protein migrated as a monomer and part of it as a dimer. However, no tetramer could be detected. In contrast, the P1L-NA$^{tet}$ protein migrated according to a tetramer with no detection of monomers or dimers. Altogether these experiments show that the NA fusion proteins are well expressed and secreted from the mammalian cells and that the presence of the bacterial Protan domain at the N-terminus did not interfere with efficient secretion of the NA-oligomeric fusion proteins (as observed for HA-oligomeric fusion proteins with Protan at the C-terminus). Moreover, the GCN4 motif induces and stabilizes the oligomeric state in the NA fusion protein as was observed for HA fusion protein. Panel D: different NA-Protan fusion proteins were analyzed for their binding characteristics to BLPs. Protan P1 variants with or without linker C-terminally of the LysM domain and with and without OMD (GCN4) were allowed to bind to BLPs by incubating 150 µg (dry weight) of the particles with an excess amount of approximately 30-45 µg of the fusion proteins after which the particles were collected (lanes indicated with B). The lanes indicated with S show NA which remained in the medium after binding. A mock incubation of BLPs with buffer was taken along as negative control. Then 5 µg of the BLP-fraction was analyzed by SDS-PAGE and Western blot using rabbit anti-PA90 serum (anti-Protan). No or poor binding was obtained for the P1L-NA$^{mon}$ and P1-NA$^{mon}$ fusion proteins lacking a GCN4 tetramerization motif as was observed for the HA-P1$^{mon}$ constructs. However, clearly efficient BLP binding was observed with the P1L-NA$^{tet}$ fusion protein. In contrast, the P1-NA$^{tet}$ construct that lacks a linker between the LysM domain and the OMD domain, showed poor binding. Clearly, a single LysM motif is already sufficient for efficient binding of the oligomeric Protan forms, provided that a linker domain is present between the LysM domain and the OMD.

Figure 9:
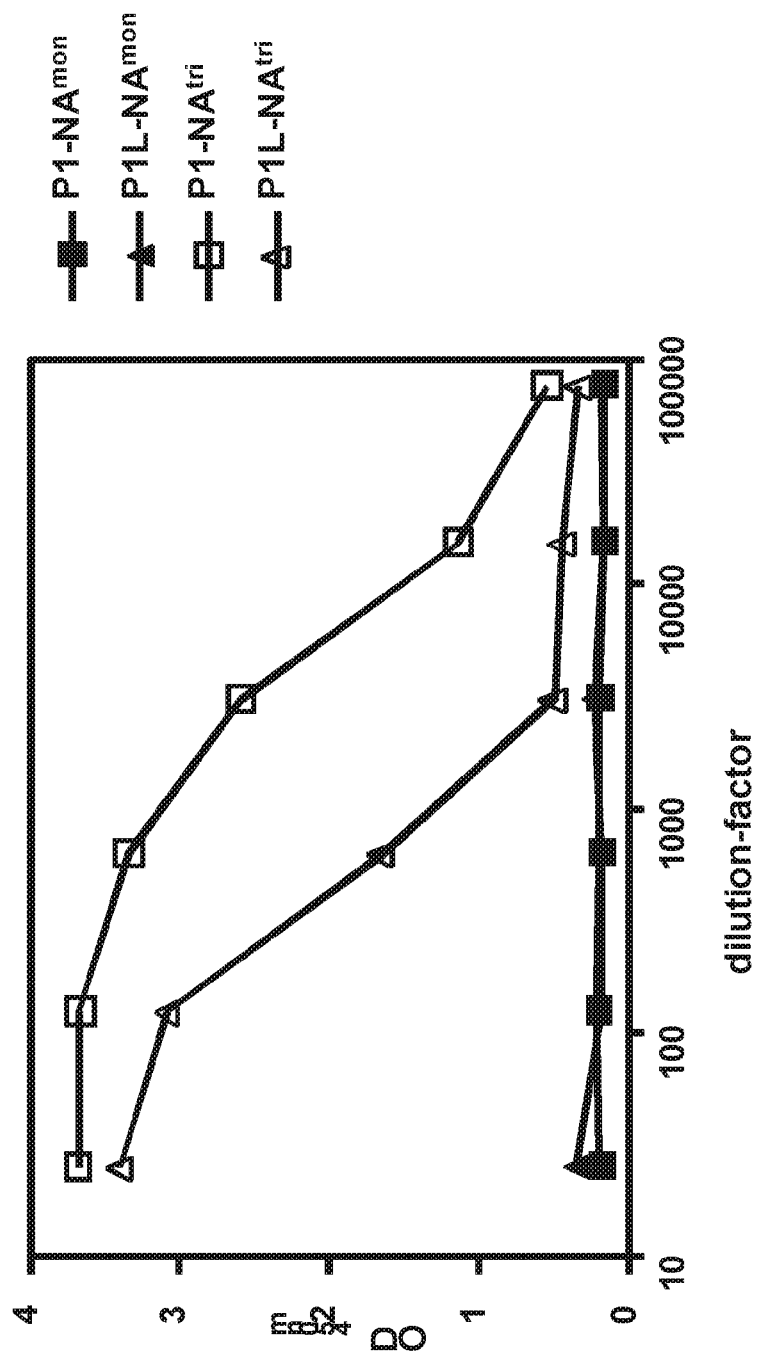

FIG. 9. Neuraminidase activity of NA variants. The neuraminidase variants P1 and P1L—both without and with GCN4—were tested for their neuraminidase activity using a fetuin-based neuraminidase activity assay. Nunc MaxiSorp 96w-plates were coated overnight at 4° C. with 100 µl of 5-µg/ml fetuin. Hundred microliters of cell culture medium samples containing similar amounts of NA (as confirmed by western blotting) were serially diluted and added to the fetuin-coated wells. After 1 h of incubation at 37° C., the plates were washed and neuraminidase activity was subsequently measured by adding peroxidase-labeled peanut agglutinin (2.5 µg/ml; Sigma), incubating for 1 h at room temperature, washing the plates, and adding 100 µl of peroxidase substrate (TMB) to each well. After 5 min, the reaction was stopped by the addition of 100 µl of 0.3 M phosphoric acid, and OD values were measured at 450 nm using an enzyme-linked immunosorbent assay (ELISA) reader (EL-808 [BioTEK]). As shown by the graphs, the Protan-NA$^{tet}$ proteins containing the GCN4 tetramerization motif exhibited a concentration dependent sialidase activity. No sialidase activity was found for the Protan-NA fusion proteins lacking the GCN4 tetramerization motif. These results clearly demonstrate that the oligomeric forms of Protan-NA are enzymatically functional.

Figure 10:
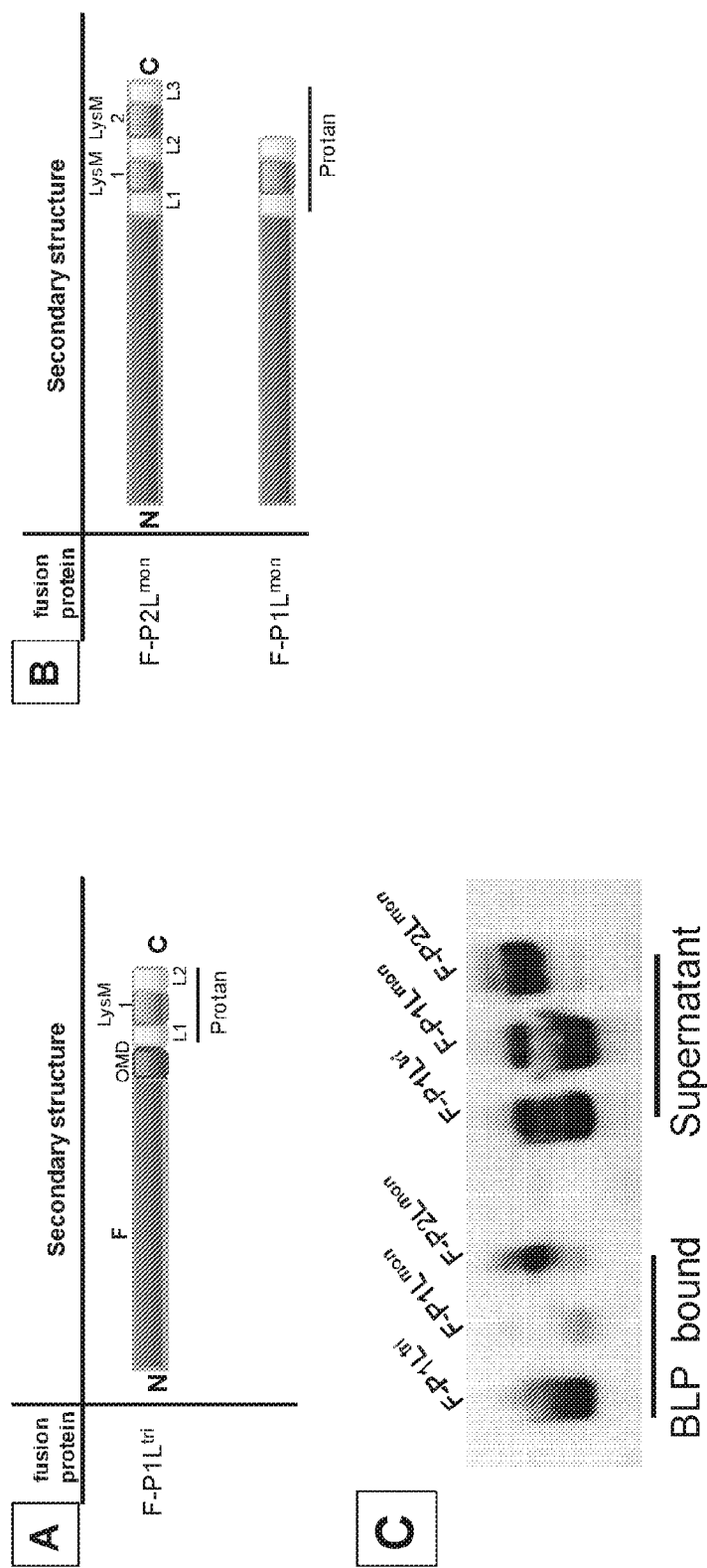

FIG. 10. Schematic representation (A and B) and expression and binding to BLPs (C) of various F fusion proteins. Schematic representation of linear F-OMD-Protan (panel A) that is able to form trimers (abbreviated as F-P$^{tri}$) and F-Protan (panel B) that exists as a monomer (abbreviated as F-P$^{mon}$). The OMD is the GCN4-pII sequence in the F constructs. The Protan part (=PBD) of the fusion varies in size. The number following the letter P in the abbreviated protein fusion name indicates the number of LysM domains in the Protan part. L1-3: linker sequences. The L following the number in the abbreviated protein fusion name indicates the presence of a C-terminal linker domain after the most C-terminal LysM domain. LysM1-2: LysM (peptidoglycan binding) domains. In panel C different F-Protan fusion proteins with and without GCN4 were compared for their binding to BLPs by incubating equal amounts of the particles in the presence of excess amounts of fusion proteins and analyzing the amounts of the BLP-bound proteins by SDS-PAGE and Western blotting. The F-P$^{tri}$ variant with one LysM and GCN4 domain and F-P$^{mon}$ variant with two LysM domains were found to bind efficiently to BLPs. Low binding efficiency to BLPs was observed for the F-P$^{mon}$ variant with one LysM domain but lacking GCN4. This result indicates that 1 LysM domain in combination with an OMD is sufficient to enable excellent binding of F proteins to BLPs, similar to what is observed for HA and NA. To study expression of the Protan-F fusion proteins, HEK 293 cells were transfected with the respective expression plasmids and incubated after which culture supernatants were harvested and cells lysed. Samples of each were analyzed by SDS-PAGE and Western blotting, using an antibody directed against the Protan moiety (α-PA90). Similar to the HA-Protan and Protan-NA proteins, all F-Protan variants were found to be secreted into the cell culture supernatant.

Figure 11:
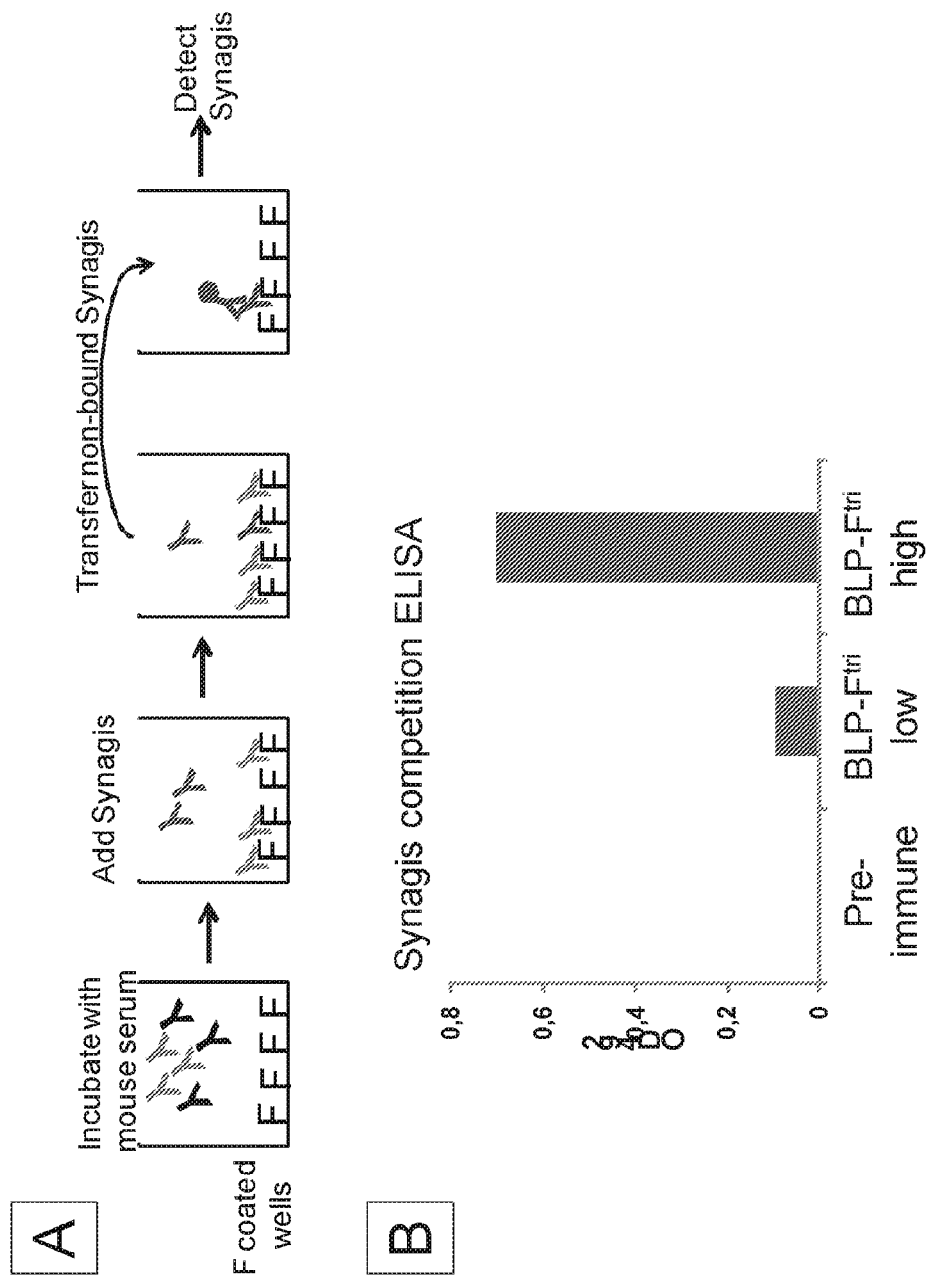

FIG. 11. Trimeric F protein bound to BLPs (BLP-F$^{tri}$) induces Synagis®-like antibody responses in mice after intranasal administration. Panel A; schematic representation of the Synagis® competition ELISA. Wells of microtiter plates are coated with F protein. These wells are incubated with two-fold serial dilutions of serum of vaccinated mice. After incubation serum dilutions are removed by washing and the wells are subsequently incubated with non-saturating amounts of Synagis®. After incubation, non-bound Synagis® is transferred to a second plate and, after binding, detected using a secondary antibody. The amount of detected bound Synagis® is a measure of the amount of Synagis®-like antibodies in the serum of the vaccinated mice. Panel B: result of the competition ELISA, which clearly shows that Synagis®-like antibodies are elicited in the serum of mice intranasally vaccinated with BLP-F$^{tri}$.

Figure 12:
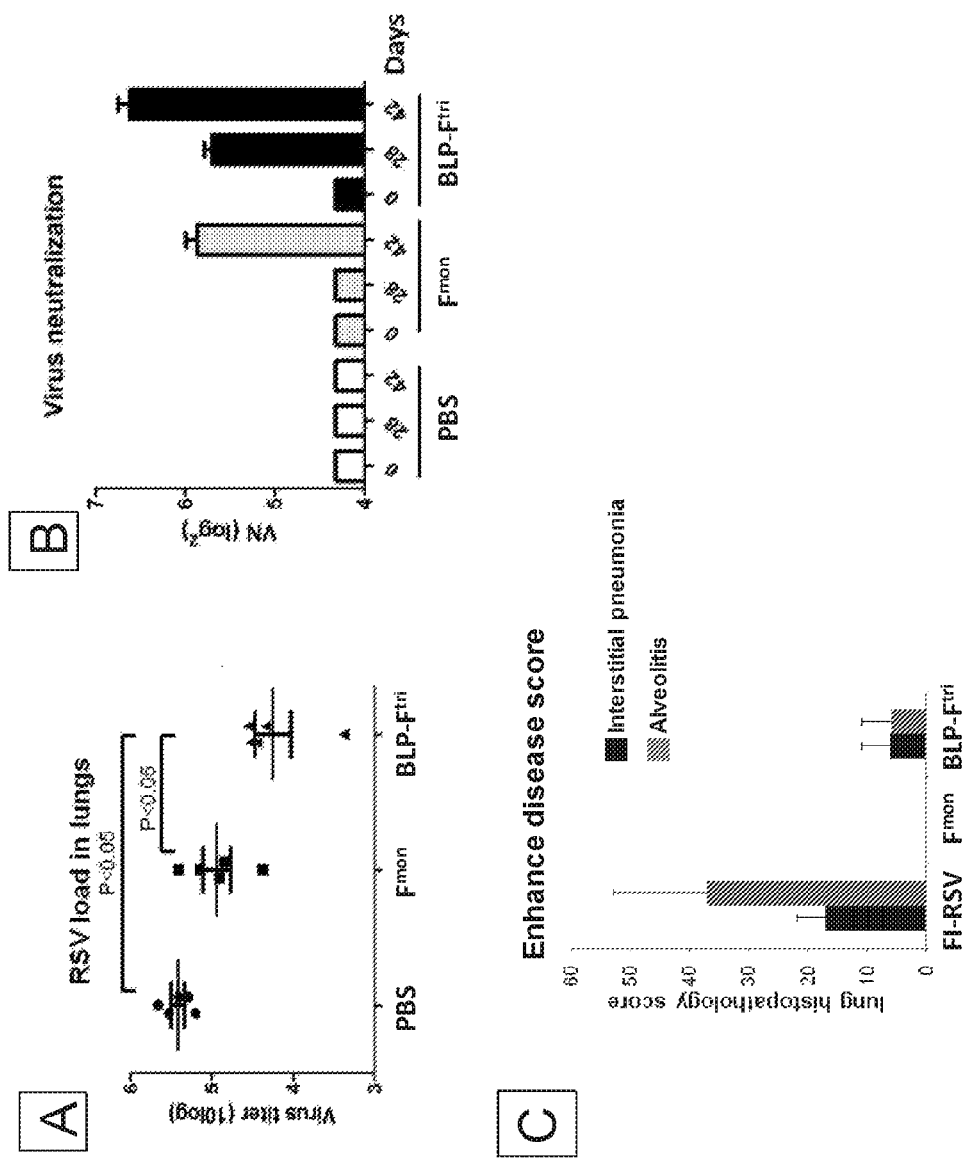

FIG. 12. Efficacy (panel A), serology (panel B) and safety (panel C) after intranasal vaccination of cotton rats with BLP-F$^{tri}$. Cotton rats were immunized three times intranasally with a 14 day interval with: (i) soluble F (F$^{mon}$) [4 µg per dose]; and (ii) trimeric F (F-P1L$^{tri}$) bound to BLPs (BLP-F$^{tri}$) [4 µg HA$^{tri}$ and 0.5 mg BLP per dose], and (iii) PBS as a negative control. Intramuscular formalin-inactivated RSV complexed with aluminium salts (FI-RSV) was given as an enhanced disease control. At day 14 after the last vaccination all animals were challenged (i.n.) with RSV/a/Long. Animals were bled for virus neutralization titers (VN) at day 0, 28 and 42. At day 5 post challenge all animals were terminated and the lungs harvested en bloc and bi-sect for viral titration and histopathology to score enhanced disease characteristics. Panel A shows a significant reduction in virus titer after BLP-F$^{tri}$ vaccination compared to F$^{mon}$ or PBS vaccination. The low virus titer coincided with the highest level of VN titers at day 28 and 42 (Panel B). Clearly, the BLP-F$^{tri}$ particulate formulation was the most immunogenic and protective formulation as compared to soluble F (F$^{mon}$) and PBS. Panel C: histopathology sections of the lungs of vaccinated cotton rats were scored for interstitial pneumonia and alveolitis. BLP-F$^{tri}$ vaccination followed by RSV infection resulted only in a low lung histopathology score compared to the scores observed after FI-RSV vaccination and subsequent RSV challenge. Clearly, the BLP-F$^{tri}$ particulate formulation does not induce enhanced disease in cotton rats.

EXPERIMENTAL SECTION

Materials and Methods 1.1. Genes and Expression Vectors

Human codon optimized genes encoding the haemagglutinin (HA) ectodomain (a.a. 17-522) of the influenza viruses A/Aichi/2/68 H3N2 (X31) and A/California/04/2009 H1N1 (H1M), the neuraminidase (NA) head domain (a.a. 75-469) of A/Mallard/Netherlands/2/2005 H5N2 (Taxonomy ID: 571469), and fusion protein (F) ectodomain of the respiratory syncytial virus (RSV) subtype A, isolate GA7SA99VR360 (a.a. 26-513) were synthesized (GenScript) and cloned into a pCD5 vector—a derivative of expression plasmid S1-Ig (Li et al., Nature 426 [2003], 450-454)—for expression in HEK293T cells.

The HA gene was flanked by sequences encoding N-terminally a CD5 signal sequence and C-terminally the artificial GCN4 trimerization sequence (GCN4-pII) (Harbury et al., Science 262 [1993], 1401-1407) followed by one of four Protan domain variants (FIG. 1A). Three of these constructs proved to express and bind to BLPs well and for these variants a construct lacking the trimerization sequence was also constructed (FIG. 1B). The NA gene was flanked by sequences encoding an N-terminal CD5 signal sequence followed by the P1 or P1L Protan domain and an artificial GCN4 tetramerization sequence (GCN4-pLI) (Harbury et al., Science 262 [1993], 1401-1407) (FIG. 8A). Based on these constructs, two additional constructs were generated lacking the artificial GCN4 tetramerization sequence (FIG. 8A). The F gene was flanked by sequences encoding N-terminally a CD5 signal sequence and C-terminally the artificial GCN4 trimerization sequence (GCN4-pII) (Harbury et al., Science 262 [1993], 1401-1407) followed by one Protan domain (FIG. 10A). Two constructs lacking a trimerization sequence followed by one or two Protan domains were also constructed (FIG. 10B).

1.2 Protein Expression and Binding to BLPs

HEK293T cells were transfected with the pCD5 expression vectors containing the HA, F or NA encoding sequences using polyethyleneimine (PEI) in a 1:5 ratio (μg DNA:μg PEI). At 6 h post transfection the transfection medium was replaced by 293 SFM II expression medium (Invitrogen), supplemented with sodium bicarbonate (3.7 g/liter), glucose (2.0 g/liter), Primatone RL-UF (3.0 g/liter, Kerry BioScience, Zwijndrecht, The Netherlands), penicillin (100 units/ml), streptomycin (100 μg/ml), glutaMAX (Gibco), and 1.5% DMSO. Tissue culture supernatants were harvested 5-6 days post transfection. HA-Protan and Protan-NA protein expression was confirmed by Western blotting using the Protan (LysM) specific polyclonal rabbit antiserum α-PA90 as a primary antibody, a swine-α-rabbit conjugated with horse radish peroxidise (Dako) as secondary antibody and detection using ECL™ (Amersham™, GE Healthcare).

Secreted HA-Protan, F-Protan or Protan-NA proteins were selectively bound to BLPs by adding 0.15 mg BLPs (dry weight) to an excess of cleared HEK293T expression culture supernatant and incubating for 30 minutes at room temperature while mixing gently. BLPs with bound protein were then collected by low-speed centrifugation and the pellet was washed three times with DPBS. Finally the pellet was resuspended in a volume of DPBS equal to the original volume of BLPs added. Binding of the HA, F and NA fusion proteins to the BLPs was assessed by SDS-PAGE and Western blotting using the α-PA90 antiserum, whereas the amount of BLP-bound protein was determined by SDS-PAGE and subsequent Coomassie blue staining using purified BSA as a reference protein.

The oligomeric state of the fusion proteins was determined by electrophoresis in blue-native gels and subsequent Western blotting using α-PA90.

1.3 Biological Characterization of Recombinant HA-Protan and Protan-NA Fusion Proteins.

Biological activity of BLP-bound HA was assessed by haemagglutination assay using chicken or turkey erythrocytes. Only with functional trimeric HA protein bound to their surface, BLPs will mediate the formation of a network ('mesh') of cross-linked erythrocytes, a process known as agglutination. Trimeric HA or BLP alone will not cross-link the erythrocytes. In the assay, 25 μl of soluble HA-Protan, BLP-bound HA or BLPs was serially diluted in 25 μl DPBS+1% BSA in a 96-well (V-shaped CellStar©, Greiner Bio-One). From the last dilution 25 μl was discarded in order to obtain equal volumes in all wells. To all wells an equal volume of 0.5% chicken erythrocytes was added, the suspensions were gently mixed and incubated for 45 minutes at 4° C. to allow cross-linking and/or precipitation of the erythrocytes.

Functionality of the soluble Protan-NA fusion proteins was assessed using a fetuin solid phase assay (Lambre et al. Clin. Chim. Acta [1991] 198:183-193). Nunc MaxiSorp 96-well plates were coated overnight at 4° C. with 100 μl of 1 μg/ml fetuin. Cleared HEK293T expression culture supernatants containing similar quantities of Protan-NA fusion proteins (based on amounts of Protan as determined by Western blotting) were serially diluted in PBS-Ca/Mg [0.901 mM/0.493 mM] after which 100 μl of the mixture was added to the fetuin-coated wells. After 1 h incubation at 37° C., the plates were washed and neuraminidase activity was subsequently measured by adding peroxidase-labelled peanut agglutinin (2.5 μg/ml; Sigma), incubating for 1 h at room temperature, washing the plates and adding 100 μl of peroxidase substrate (TMB) to each well. After 5 minutes, the reaction was stopped by the addition of 100 μl of 0.3 M phosphoric acid and OD values were measured at 450 nm using an ELISA reader (EL-808 [BioTEK]).

1.4 Immunizations of Mice with Oligomeric Protein Formulations.

Four groups of ten female Balb/c mice of 6-8 week old were immunized three times intranasally with a 10 day interval, with 4 different HA formulations (H1M): (i) soluble trimeric HA ($HA^{tri}$) [1 μg per dose]; (ii) soluble trimeric HA mixed with BLP (BLP+$HA^{tri}$) [1 μg $HA^{tri}$ and 0.3 mg BLP per dose]; (iii) trimeric HA (HA-P1$L^{tri}$) bound to BLPs (BLP-$HA^{tri}$) [1 μg $HA^{tri}$ and 0.3 mg BLP per dose], and (iv) monomeric HA (HA-P2$L^{mon}$) bound to BLPs (BLP-$HA^{mon}$) [1 μg $HA^{mon}$ and 0.3 mg BLP per dose]. Fourteen days post the $3^{nd}$ immunization, serum and nasal washes were collected for ELISA analysis to determine the anti-H1M IgG (serum samples) and anti-H1M S-IgA (nasal wash) response. For this purpose, plates were coated with 200 ng HA (H1M) per well. Serial dilutions of the sera were incubated for 90 min and binding of H1M-specific IgG and IgA, respectively, was detected using anti-mouse IgG and IgA-HRP conjugates (Southern Biotech). For a calibration curve mouse IgG was diluted in triplicate (first well 0.5 μg/mL) (mouse IgG1, Sigma) (only for serum IgG). After staining, the absorbency at 492 nm was determined in an ELISA microtiter plate reader. To calculate the specific anti-HA IgG antibodies in serum (expressed in μg/mL) the calibration curve is used (parameters of curve determined by 4-parameterfit). To calculate the specific anti-HA IgA antibodies in nasal wash (expressed in titers which are the reciprocal of the calculated sample dilution corresponding with an A492=0.3 after background correction) the parameters of the curve were determined by 4-parameterfit. HA-specific haemagglutination inhibition titres (HI) were determined using serum collected on day 34 (each individual animal) of each group. The serum samples were inactivated at 56° C. for 30 min and subsequently overnight at RT incubated with kaolin to reduce a-specific haemagglutinin inhibition. The kaolin treated samples were applied onto the plates in duplicate in serial two-fold dilutions using a multichannel pipette and mixed with the appropriate homologous inactivated Influenza virus (A/California/07/2009 (H1N1), 4 HAU; NIBSC, UK) and incubated for 40 min at RT. Subsequently, a 1% guinea pig erythrocyte solution was added to each well. Haemagglutinin was allowed to proceed for two hours and scored for the highest dilution at which haemagglutination was observed.

Two groups of ten female Balb/c mice of 6-8 week old were immunized three times intranasally with a 10 day interval, with 2 different BLP-$F^{tri}$ formulations: (i) F bound to BLPs (BLP-$F^{tri}$ low) [0.6 μg $F^{tri}$ and 0.5 mg BLP per dose]; and (ii) F bound to BLPs (BLP-$F^{tri}$ high) [2.2 μg $F^{tri}$ and 0.5 mg BLP per dose]. Fourteen days post the 3$^{rd}$ immunization, serum samples were collected and pooled per group for a Synagis® competition ELISA analysis to determine the level of Synagis®-like antibodies induced. For this purpose, plates were coated with 100 ng F per well. Serial dilutions of the sera (including pre-immune serum) were incubated for 90 min followed by a wash. Next, the plates were incubated with sub-saturating amounts of Synagis®. After incubation, non-bound Synagis® was transferred to a second F coated plate and, after binding, detected using a secondary anti-human IgG antibody. The color development was measured at 492 nm.

1.5 Immunizations of Cotton Rats with Oligomeric F-Protan and Subsequent Challenge with RSV.

Four groups of 5 young adult cotton rats (6-8 weeks of age) were immunized three times with a 14 day interval with 4 different formulations: (i) PBS (negative control), (ii) soluble monomeric F ($F^{mon}$) [4 μg per dose]; (iii) trimeric F (F-P1L$^{tri}$) bound to BLPs (BLP-$F^{tri}$) [4 μg HA$^{tri}$ and 0.5 mg BLP per dose], and (iv) formalin-inactivated RSV vaccine formulated in aluminium salts (FI-RSV) [Lot#100 (1:125)]. Group 1 to 3 were vaccinated intranasally and group 4 intramuscularly.

At day 0, 28 and 42 serum was collected for virus neutralization analysis. For this purpose, heat inactivated serum is serial diluted in a 96 well plate. To each well 25 to 50 plaque forming units (PFU) is added. The dilution plates are incubated for 1 hour at 25-30° C. to allow the serum samples and virus to interact. Next the virus serum mix is transferred to HEp-2 cells for virus titration. The cells are incubated with mix for 1 h followed by the addition of a methyl cellulose overlay. The cells are incubated 4 days at 37° C. after which the overlay is removed. Crystal violet stain is added and allowed to fix for 2 to 4 hours at 25-30° C. The stain is removed by rinsing with cold water. Next the plates are allowed to air dry completely prior to reading. The number of plaque forming units (PFU) per well using a dissecting microscope. At day 42 each animal were challenged with 100 μL of RSV/A/Long at 10$^5$ pfu per animal. At day 5 post challenge the animals were terminated and the lungs were harvested en bloc and bi-sect for viral titration (left section) and histopathology (right section). Histopathology sections were scored for interstitial pneumonia and alveolitis.

Example 1

Expression of the HA-Protan, F-Protan and Protan-NA Fusion Proteins

In order to express soluble HA-Protan, F-Protan and Protan-NA chimeric proteins in mammalian cells, the ectodomain-coding sequences were first cloned into appropriate expression vectors. In the pCD5 vector expressing the HA-Protan fusion proteins, the HA-ectodomain sequence was preceded by a signal peptide-encoding sequence, to allow efficient secretion of the recombinant protein, and followed by a sequence encoding one of four Protan domain variants and an artificial GCN4 trimerizaton motif (GCN4-pII; OMD) between the HA and Protan domain variants (FIG. 1A). For the three HA-Protan fusion protein variants that were most efficiently expressed and secreted (see below) we also constructed and expressed fusion proteins that lacked the GCN4 trimerization sequence (OMD; FIG. 1B).

In the pCD5 vector expressing the Protan-NA chimeric proteins, the NA-head domain sequence was preceded by a signal peptide-encoding sequence, to allow efficient secretion of the recombinant protein, and by a sequence encoding a Protan domain variant (one LysM domain) either with or without an artificial GCN4 tetramerizaton motif (GCN4-pLI; OMD) placed in between the Protan domain and the NA sequence (FIG. 8A).

In the pCD5 vector expressing the F-Protan fusion proteins, the F-ectodomain sequence was preceded by a signal peptide-encoding sequence, to allow efficient secretion of the recombinant protein, and followed by a sequence encoding one LysM domain variant and an artificial GCN4 trimerizaton motif (GCN4-pII; OMD) between the F and the LysM domain (FIG. 10A). We also constructed and expressed two F-Protan fusion proteins that lacked the GCN4 trimerization sequence (OMD) with one and two LysM domains, respectively (FIG. 10B).

Expression of the HA-Protan, F-Protan and Protan-NA fusion proteins with or without an artificial trimeric, trimeric or tetrameric GCN4 multimerization motif (OMD), respectively, was achieved by transfection of the expression plasmids into HEK293 cells. Expression and secretion of the HA-Protan, F-Protan and Protan-NA proteins was verified by subjecting cell culture supernatants to gel electrophoresis followed by Western blotting using an antibody directed against the Protan moiety (α-PA90). HA-Protan fusion proteins and F-Protan fusion proteins containing the GCN4 domain (OMD) are abbreviated HA-P$^{tri}$ and F-P$^{tri}$, respectively, indicating the trimerization potential of these fusion proteins. HA-Protan and F-Protan fusions lacking the GCN4 domain (OMD) are abbreviated HA-P$^{mon}$ and F-P$^{mon}$, respectively, indicating the monomeric state of the proteins. Likewise, the Protan-NA fusions are abbreviated: P-NA$^{tet}$ for the variants containing the GCN4 domain (OMD) indicating the tetramerization potential of the fusion protein and P-NA$^{mon}$ for variants lacking the GCN4 domain (OMD) indicating the monomeric state of the protein. All HA-P variants of both X31 and H1M influenza virus derived HAs were readily expressed and efficiently secreted into the cell culture medium with only minimal retention of the fusion protein in the cells, as shown in FIG. 7A for the HA-P$^{tri}$ variants. The X31 HA-P$^{tri}$ fusion proteins were produced somewhat less abundant as compared to HA-P$^{tri}$ proteins of H1M. While HA-species differences in expression levels may occur, in general it seems that HA fused to P1L and P2L display the highest production levels with the most limited retention of fusion protein in the cells compared to the P1 and P2 variants, respectively. Similar to the HA-Protan proteins, all Protan-NA and F-Protan variants were found to be secreted into the cell culture supernatant (FIG. 8B and 10C). Only some limited intracellular retention was observed for the Protan-NA variants containing the GCN4 tetramerization motif (FIG. 8B).

Clearly, the presence on the N- or C-terminus of the bacterial Protan domain variants did not interfere with efficient secretion of the HA- and NA-oligomeric fusion proteins by the mammalian expression cells.

Example 2

Binding of HA-GCN-Protan, F-GCN-Protan and Protan-GCN-NA Fusion Proteins to BLPs The binding characteristics of the various HA-Protan, F-Protan and Protan-NA fusion proteins to BLPs were determined by comparing binding to BLPs in the presence of excess amounts of the various Protan fusion proteins. The SDS-PAGE and Western blotting analyses demonstrated that all HA-P$^{tri}$ variants bound. The GCN4 domain strongly enhances the binding properties of single LysM domain (1L) constructs. This was demonstrated in an experiment with several HA-P constructs that were bound to BLPs. FIGS. 1C and D show three HA-Protan variants lacking the OMD GCN4 that were tested in duplicate: Protan variant P2L$^{mon}$, Protan variant P1L$^{mon}$ and Protan variant P1$^{mon}$ in comparison to the GCN4-containing HA-Protan fusion protein with Protan variant P1L$^{tri}$. The results of the Coomassie staining (panels I) consistently demonstrate poor (H1M) or hardly any (X31) binding when the extension contained just one LysM domain in the monomeric constructs lacking a GCN4 domain (P1L$^{mon}$ and P1$^{mon}$). More efficient binding occurred when the monomeric fusion protein had 2 LysM domains (P2L$^{mon}$) as expected. In contrast, in case of the HA-Protan fusion protein with GCN4, efficient binding was already achieved with 1 LysM domain (P1L$^{tri}$). Clearly, unlike for monomeric HA-Protan fusion proteins, a single LysM motif is already sufficient for efficient binding of the trimeric HA-Protan forms.

In another experiment, the binding efficiency of an HA construct with a single LysM domain combined with an OMD (HA-GCN4-P1L or HA-P1L$^{tri}$) was compared with a monomeric HA construct with two LysM domains (FIG. 3). For this purpose, increasing amounts (0-4 µg) of HA-P1L$^{tri}$ and HA-P2L$^{mon}$ which both showed efficient binding to BLPs (see FIG. 1C/D) were allowed to bind to a fixed amount (0.3 mg) BLPs. More HA-P1L$^{tri}$ bound to BLPs at similar concentrations as used for HA-P2L$^{mon}$. Hence, binding of proteins to BLPs using a single LysM domain combined with an OMD such as GCN4 in an oligomeric construct is more efficient than with two LysM domains in a monomeric construct.

In another experiment (FIG. 5A) the stability of the binding of HA-GCN4-P1L to BLP was assessed upon long term storage in PBS at 2-8° C. The data show that an HA construct with a single LysM domain combined with an OMD remains stably bound to BLPs for at least 9 months. This is in strong contrast to the observations of Raha et al. (2005) and Moeini et al. (2011) whose experiments showed a loss of proteins bound with single LysM domain to bacteria of over 40% within 5 days of storage.

BLP-binding of the different Protan-NA and F-Protan fusion proteins corroborated the observations with the HA constructs that a single LysM domain combined with an OMD results in efficient binding. In FIGS. 8D and 10C, no or poor binding was obtained for the P1L-NA$^{mon}$, P1-NA$^{mon}$ and P1L-F$^{mon}$ fusion proteins lacking a GCN4 multimerization motif as was observed for the HA-P1$^{mon}$ constructs. However, clearly efficient BLP binding was observed with the F-P1L$^{tri}$, F-P2L$^{mon}$ and P1L-NA$^{tet}$ fusion proteins.

As a control we showed that the OMD itself does not enable binding to BLP particles. For this purpose, binding of HA-Strep$^{tri}$, which carries a Strep-tag instead of a Protan extension, and HA-1L$^{tri}$ to BLP particles was compared. FIG. 7C shows a Western blot in which HA-Strep$^{tri}$ (lane 3) was mixed with BLPs. The BLPs were recovered and loaded on the gel (lane 4). No binding of HA-Strep$^{tri}$ occurred. In contrast, efficient binding was observed for HA-1L$^{tri}$ (compare lanes 5 and 6).

In addition, both for the H1M (FIG. 1C) and for the X31 virus derived HA proteins (FIG. 7B), variants HA-P1$^{tri}$, HA-P1L$^{tri}$ and HA-P2L$^{tri}$ bound to the BLPs most efficiently. Low binding efficiency was observed for the H1M1 and X31 HA-P2$^{tri}$ proteins to BLPs. This was also observed for the P1-NA$^{tet}$ construct that lacks a linker between the LysM domain and the OMD domain, which showed poor binding. Clearly, a linker domain between the LysM domain and the OMD is needed for proper binding to BLPs.

In the natural situation as observed in the monomeric AcmA, 3 consecutive intramolecular LysM domains (in cis) facilitate efficient binding. Reduction of this number to 1 LysM domain results in a strong reduction of binding efficacy (Bosma et al. [2006]) and low stability (Raha et al. [2005] and Moeini et al. [2011]). Taken together, our results indicate that a single LysM domain can facilitate highly efficient and stable binding to BLPs when placed in an multimeric intermolecular conformation (LysM domains interacting in trans) where the subunits, each containing a single LysM domain, are multimerized by an OMD. Moreover, a linker domain present between the LysM domain and the OMD further increases the production and binding efficacy.

The use of a single LysM domain has several advantages: (i) it reduces the size of the binding domain and, (ii) it prevents binding of immunogenic inferior monomeric fusions as can still be the case when 2 or more LysM domains are used (HA-P1L$^{mon}$ does not bind vs HA-P2L$^{mon}$ binds to BLPs, see FIGS. 1C and D, panels I and II; F-P1L$^{mon}$ does not bind vs HA-P2L$^{mon}$ binds to BLPs, see FIG. 10C). Hence, a single LysM domain facilitates the selective binding of the immunogenic most relevant (i.e. multimeric) forms of the fusion proteins (see FIG. 2).

Example 3

Functionality of the HA-GCN-Protan and Protan-GCN-NA Fusion Proteins

Oligomeric State of the Fusion Proteins

The oligomeric state of the HA-Protan and Protan-NA proteins with or without an artificial OMD, the trimeric of tetrameric GCN4 multimerization motif, respectively, was analyzed by blue-native gel electrophoresis. Samples of HA-Protan fusion proteins that had been shown to bind to BLPs, i.e. the H1M virus derived HA-P1$^{tri}$ and HA-P1L$^{tri}$ proteins were boiled for 10 seconds, 30 seconds or 3 minutes in order to dissociate HA trimers. All the HA-P$^{tri}$ proteins migrated in the gel with a mobility according to that of a trimer when heated briefly (boiling for 10 sec) and these HA-trimers dissociated into dimeric and monomeric forms of HA after prolonged sample boiling (FIG. 1E, left panels). HA-P1$^{tri}$ and HA-P1L$^{tri}$ trimers remained detectable even after prolonged boiling of the samples. In contrast, all the equivalent HA-P$^{mon}$ variants migrated with the mobility of a monomer. In addition, most of these HA-P$^{mon}$ proteins exhibited a variable, but sometimes strong tendency to form high molecular weight aggregates (FIG. 1E, right panels, indicated by the asterisks), most likely as a result of the poor folding and stability of these non-native proteins.

Samples of the P1L-NA variants with and without GCN4 were analysed by blue-native gel electrophoresis (FIG. 8C). Most of the P1L-NA$^{mon}$ protein migrated as a monomer, part of it as a dimer, however no tetramer could be detected. The P1L-NA$^{tet}$ protein migrated according to a tetramer with no detection of monomers or dimers.

These data clearly demonstrate that the presence of an OMD such as the GCN4 motif is required to obtain stable oligomeric proteins that have the native quaternary structure.

Biological Activity of the Fusion Proteins

The biological activity of native HA as present in particles can be assessed by a haemagglutination assay using erythrocytes (FIG. 4A). With this assay the sialic acid receptor binding function of the HA protein—a biological property only exhibited by trimeric HA—is assessed. In order to demonstrate that agglutination in the described assay is critically dependent on the presence of HA oligomers bound to BLPs rather than on HA monomers bound to BLPs, HA-P1L$^{tri}$ and HA-P2L$^{mon}$ (both H1M) were bound to BLPs. FIG. 4B clearly shows that HA-P1L$^{tri}$ bound to BLPs is able to cause agglutination of the red blood cells in a concentration dependent way (lanes 3-6), while HA-P2L$^{mon}$ bound to BLPs is not able to cause agglutination (lanes 8-11). These results clearly show that only oligomeric forms of HA bound to BLPs are biologically active.

The biological functionality of soluble monomeric and oligomeric P1-NA and P1L-NA proteins was studied by measuring their sialidase activity using a solid phase binding assay with the sialidated blood glycoprotein fetuin as the substrate. Desialylation by Protan-NA was measured by means of the PNA lectin binding activity as detailed in the Material and Methods section. As shown in FIG. 9, the Protan-NA$^{tet}$ proteins containing the GCN4 tetramerization motif exhibited a concentration dependent sialidase activity. No sialidase activity was found for the Protan-NA fusion proteins lacking the GCN4 tetramerization motif (P-NA$^{mon}$). These results clearly demonstrate that the oligomeric (but not the monomeric) forms of Protan-NA are functional.

In conclusion, biologically active, soluble trimeric HA and soluble tetrameric NA proteins fused to different Protan variants were efficiently produced in mammalian cells. Efficient binding to BLPs was already achieved with 1 LysM domain, provided that the fusion protein contained an OMD, such as the GCN4 oligomerization domain; in other words, efficient binding mediated by a single LysM domain depends on—and selects for—the proteins occurring in a oligomeric state. Furthermore, the proteins bound in their oligomeric state to the BLP demonstrate a biological activity that is similar to the native proteins.

Example 4

Immunogenicity of Oligomeric HA-Protan in Particulate Form

The immunogenicity of trimeric HA (HA-P1L$^{tri}$) bound to BLPs (BLP-HA$^{tri}$) was evaluated after two intramuscular administrations in mice. The HA subtype used was H1M. The BLP-HA$^{tri}$ particulate formulation was compared to soluble trimeric HA (HA$^{tri}$) and soluble trimeric HA mixed with BLP (BLP+HA$^{tri}$). The amount of HA$^{tri}$ in the formulations was 0.33 µg per dose. Ten days post 2nd immunization serum was collected and pooled per group for ELISA analysis to determine the anti-H1M IgG response. The results in FIG. 6A clearly show that BLP-HA particulate formulations were the most immunogenic formulation with respect to serum HA-specific IgG responses as compared to soluble trimeric HA (HA$^{tri}$) and soluble trimeric HA mixed with BLP (BLP+HA$^{tri}$). Highly relevant however, is the observation (FIG. 6B) that the trimeric HA bound to BLPs (BLP-HA$^{tri}$) elicits higher functional antibody titers compared to monomeric HA bound to BLPs (BLP-HA$^{mon}$) measured as hemagglutination inhibition (HI) titers. In addition, only trimeric HA bound to BLPs (BLP-HA$^{tri}$) elicits significant levels of HA-specific secreted IgA (S-IgA) in the mucosal secretions of the nose (FIG. 6C). These results are most likely a reflection of the proper folding and functionality of the trimeric HA bound to BLPs (BLP-HA$^{tri}$).

Hence, particulate BLP formulations that contain bound native oligomeric antigen compositions, established through the use of an OMD and a single LysM domain, are highly immunogenic and elicit more potent, and a qualitatively more relevant response than soluble oligomeric and monomeric bound formulations.

Example 5

Immunogenicity, Efficacy and Safety of Oligomeric F-Protan in Particulate Form

The immunogenicity of trimeric F (HA-P1L$^{tri}$) bound to BLPs (BLP-F$^{tri}$) was evaluated after three intranasal administrations in mice. Three doses (0.6 and 2.2 µg per dose) of the BLP-F$^{tri}$ particulate formulation were used. Ten days post 3$^{rd}$ immunization, serum was collected and pooled per group for a Synagis® competition ELISA analysis (FIG. 11A) to determine the anti-F antibody response. In this assay, antibodies elicited in the mice by the vaccines that bind to F epitopes recognized by the neutralizing Synagis® antibody, prevent the binding of Synagis®. Thus the measured amount of non-bound Synagis® in the assay is a measure of Synagis®-like antibodies raised by the vaccines. The results in FIG. 11B clearly show that the trimeric F bound to BLPs (BLP-F$^{tri}$) elicits Synagis®-like antibodies in a dose dependent manner. Pre-immune sera were negative, as expected.

In conclusion, particulate BLP formulations that contain bound native oligomeric F antigen, established through the use of an OMD and a single LysM domain, are highly immunogenic and elicit neutralizing-type antibodies.

The cotton rat closely recapitulates the devastating pathological outcome, known as enhanced disease, associated with the RSV-vaccine failure in the 1960's. In the 1960s, trials in infants were conducted in the USA with formalin-inactivated RSV vaccine formulated in aluminium salts (FI-RSV). During subsequent natural RSV exposure, the rate of the virus infection in infants who received the vaccine was no less (and was perhaps even greater) than that in control group immunised with parainfluenza vaccine. Most remarkably, 80% of RSV vaccinees needed hospitalisation, whereas only 5% of such infections among control parainfluenza vaccinees required admission to the hospital. Two of the vaccinated infants died. Thus, rather than protecting, FI-RSV was an infamous vaccine candidate that primed young infants for exacerbated disease upon exposure to natural RSV infection. Administration of FI-RSV to cotton rats followed by RSV infection results in comparable enhanced (lung) pathology characterized by interstitial pneumonia and alveolitis. For this reason safety testing (absence of enhanced disease) of a concept RSV vaccine in cotton rats is essential step in RSV vaccine development.

The efficacy and safety (lack of enhanced disease symptoms) of trimeric F (HA-P1L$^{tri}$) bound to BLPs (BLP-F$^{tri}$) was evaluated after three intranasal administrations in cotton rats and was compared to monomeric F (F$^{mon}$). The capacity of the serum antibodies raised by the vaccines to inhibit RSV replication was determined in virus neutralization assays in samples taken 14 days after each vaccine administration. For the evaluation of safety, formalin-inactivated RSV vaccine formulated in aluminium salts (FI-RSV) was given intramuscularly to an additional group of animals. FI-RSV is known to elicit pathology in the lungs of cotton rats that is related to signs of enhanced disease (interstitial pneumonia and alveolitis). Fourteen days after the final immunizations each animal was challenged with RSV. At day 5 post challenge the animals were terminated and the lungs were harvested for determination of virus titers, virus neutralization titers and scoring of interstitial pneumonia and alveolitis by histopathology. The results clearly show (FIG. 12A) that trimeric F (HA-P1L$^{tri}$) bound to BLPs (BLP-F$^{tri}$) is more efficacious in reducing the lung viral titers as compared to monomeric F (F$^{mon}$). This observation correlates very well with the higher virus neutralizing capacity of sera from animals immunized with BLP-F$^{tri}$ compared to that of F$^{mon}$ (FIG. 12B). Importantly, the increased efficacy of the trimeric F (HA-P1L$^{tri}$) bound to BLPs (BLP-F$^{tri}$) is associated with lack of signs of enhanced disease (interstitial pneumonia and alveolitis in the lungs), which is typical for the use of FI-RSV in this model (FIG. 12C).

In conclusion, particulate BLP formulations that contain bound native oligomeric F antigen, established through the use of an OMD and a single LysM domain, are highly efficacious, elicit virus neutralizing antibodies and have a favourable safety profile.

INCORPORATION OF SEQUENCE LISTING

Incorporated herein by reference in its entirety is the Sequence Listing for the application. The Sequence Listing is disclosed on a computer-readable ASCII text file titled, “sequencelisting294-430PCTUS.txt”, created on Nov. 25, 2013. The sequencelisting294-430PCTUS.txt file is 3.27 kb in size.

The invention claimed is:

1. An immunogenic composition in particulate form, comprising:
   i. a non-viable bacterium-like particle (BLP) obtained from a Gram-positive bacterium as particulate carrier;
   ii. oligomers of a recombinantly produced polypeptide attached non-covalently to said BLP, wherein the recombinant polypeptide comprises:
      A) an N- or C-terminal antigenic domain, comprising at least one surface exposed polypeptide of pathogenic or tumour origin, or antigenic part thereof, the antigenic domain being fused to
      B) an oligomerization domain (OMD), said oligomerization domain being fused via
      C) a linker domain to
      D) a peptidoglycan binding domain (PBD) consisting of a single copy of a LysM domain mediating the non-covalent attachment of the polypeptide to the BLP, and wherein the polypeptide as a whole contains only a single copy of a LysM domain; and
   iii. a pharmaceutically acceptable diluent or excipient.

2. The immunogenic composition according to claim 1, wherein the surface exposed polypeptide in the antigenic domain of said recombinant polypeptide comprises an ectodomain of an enveloped virus protein.

3. The immunogenic composition according to claim 2, wherein said virus protein is from a virus selected from the group of viruses consisting of influenza virus, animal corona virus, human respiratory corona virus, human immunodeficiency virus (HIV), and parmixovirus.

4. The immunogenic composition according to claim 2, wherein said virus protein is from a virus is selected from the group of viruses consisting of syncytial virus (RSV) or metapneumovirus.

5. The immunogenic composition according to claim 2, wherein the surface exposed polypeptide or antigenic part thereof is selected from the group consisting of influenza hemagglutinin (HA) ectodomain or part thereof, influenza neuraminidase (NA) ectodomain or part thereof, coronavirus spike (S) protein ectodomain or part thereof, RSV glycoprotein F or G ectodomains or parts thereof and HIV gp140 ectodomain or part thereof.

6. The immunogenic composition according to claim 1, wherein said linker domain of said recombinant polypeptide consists of between 10 and 60, amino acids.

7. The immunogenic composition according to claim 6, wherein the linker domain comprises an amino acid sequence selected from the group consisting of:

```
                                        (SEQ ID NO. 4)
GASSAGNTNSGGSTTTITNNNSGTNSSST, (SEQ ID NO. 5)
GSASSTNSGGSNNSASTTPTTSVTPAKPTSQ,
and (SEQ ID NO. 6)
QSAAASNPSTGSGSTATNNSNSTSSNSNAS.
```

8. The immunogenic composition according to claim 1, wherein the oligomerization domain (OMD) of said recombinant polypeptide is a dimerization, trimerization or tetramerization domain.

9. The immunogenic composition according to claim 1, wherein the recombinant polypeptide furthermore comprises, in case of an N-terminal antigenic domain a C-terminal capping sequence, or in case of a C-terminal antigenic domain an N-terminal capping sequence.

10. The immunogenic composition according to claim 1, wherein said bacterium is a non-pathogenic bacterium.

11. The immunogenic composition according to claim 1, wherein the particulate carrier is provided non-covalently with at least a first oligomer of polypeptides comprising surface exposed polypeptides or antigenic parts thereof derived from a first pathogen and a second oligomer of polypeptides comprising surface exposed polypeptides or antigenic parts thereof derived from a second pathogen.

12. Method for providing an immunogenic composition claim 1 comprising the steps of:
   a) providing a recombinant polypeptide as recited in claim 1, comprising culturing a host cell comprising an expression vector encoding said polypeptide in a suitable medium allowing for expression of the polypeptide, and isolating the polypeptide;
   b) providing a non-viable bacterium-like particle (BLP) obtained from a Gram-positive bacterium,
   c) allowing for non-covalent binding of said polypeptide(s) to said BLP to form an immunogenic complex comprising oligomers of a surface exposed polypeptide of pathogenic origin or antigenic part thereof bound non-covalently to a particulate carrier, and
   d) formulating the immunogenic complex into an immunogenic composition.

13. A method for eliciting an immune response against a pathogen in an individual comprising administering to said individual an immunogenic composition according to claim 1.

14. Method according to claim 13, for eliciting an immune response against a viral disease in an individual, preferably wherein the viral disease is caused by influenza virus, animal coronavirus, human respiratory coronaviruses, human immunodeficiency virus (HIV), or paramyxovirus, in particular respiratory syncytial virus (RSV) or metapneumovirus.

15. The immunogenic composition according to claim 1, wherein said linker domain of said recombinant polypeptide consists of between 20 and 50 amino acids.

16. The immunogenic composition according to claim 1, wherein said linker domain of said recombinant polypeptide consists of between 25 and 40 amino acids.

17. The immunogenic composition according to claim 1, wherein said linker domain of said recombinant polypeptide consists of 30 amino acids.

18. The immunogenic composition according to claim 1, wherein the oligomerization domain (OMD) of said recombinant polypeptide is a GCN4 based dimerization, trimerization, or tetramerization domain; C-terminal domain sequence of T4, cipritin (foldon), or a functional part or analog thereof (C-terminal 27-30 residues); or the soluble trimerization domain of chicken cartilage matrix (CART) protein.

19. The immunogenic composition according to claim 1, wherein said bacterium is a food-grade bacterium.

20. The immunogenic composition according to claim 1, wherein said bacterium is selected from the group consisting of *Lactococcus*, a *Lactobacillus*, a *Bacillus* and a *Mycobacterium* ssp.

21. A recombinant polypeptide comprising:
    A) an N- or C-terminal antigenic domain, comprising at least one surface exposed polypeptide (e.g. of pathogenic or tumour cell origin) or antigenic part thereof, the antigenic domain being fused to
    B) an oligomerization domain (OMD), said oligomerization domain being fused via
    C) a linker domain to
    D) a peptidoglycan binding domain (PBD) consisting of a single copy of a LysM domain capable of mediating the non-covalent attachment of the polypeptide to a peptidoglycan carrier particle being a non-viable bacterium-like particle (BLP) obtained from a Gram-positive bacterium, and wherein the polypeptide as a whole contains only a single copy of a LysM domain.

22. A nucleic acid sequence encoding a polypeptide according to claim 21.

23. A vector comprising a nucleic acid sequence according to claim 22.

24. A host cell, comprising a nucleic acid sequence according to claim 22, preferably wherein said host cell is a eukaryotic host cell, more preferably a mammalian host cell.

25. A host cell, comprising a vector according to claim 23.

* * * * *

```
                         SEQUENCE LISTING

<160> NUMBER OF SEQ ID NOS: 7

<210> SEQ ID NO 1
<211> LENGTH: 32
<212> TYPE: PRT
<213> ORGANISM: Saccharomyces cerevisiae
<220> FEATURE:
<221> NAME/KEY: MISC_FEATURE
<222> LOCATION: (1)..(32)
<223> OTHER INFORMATION: GCN4-p1

<400> SEQUENCE: 1

Met Lys Gln Leu Glu Asp Lys Val Glu Glu Leu Leu Ser Lys Asn Tyr
1               5                   10                  15

His Leu Glu Asn Glu Val Ala Arg Leu Lys Lys Leu Val Gly Glu Arg
            20                  25                  30

<210> SEQ ID NO 2
<211> LENGTH: 27
<212> TYPE: PRT
<213> ORGANISM: Saccharomyces cerevisiae
<220> FEATURE:
<221> NAME/KEY: MISC_FEATURE
<222> LOCATION: (1)..(27)
<223> OTHER INFORMATION: GCN4-based trimerization

<400> SEQUENCE: 2

Met Lys Gln Ile Glu Asp Lys Ile Glu Glu Ile Glu Ser Lys Gln Lys
1               5                   10                  15

Lys Ile Glu Asn Glu Ile Ala Arg Ile Lys Lys
            20                  25

<210> SEQ ID NO 3
<211> LENGTH: 31
<212> TYPE: PRT
<213> ORGANISM: Saccharomyces cerevisiae
<220> FEATURE:
<221> NAME/KEY: MISC_FEATURE
<222> LOCATION: (1)..(31)
<223> OTHER INFORMATION: GCN4-based tetramerization domain
```

-continued

<400> SEQUENCE: 3

Met Lys Gln Ile Glu Asp Lys Leu Glu Glu Ile Leu Ser Lys Leu Tyr
1               5                   10                  15

His Ile Glu Asn Glu Leu Ala Arg Ile Lys Lys Leu Leu Gly Glu
            20                  25                  30

<210> SEQ ID NO 4
<211> LENGTH: 29
<212> TYPE: PRT
<213> ORGANISM: Saccharomyces cerevisiae
<220> FEATURE:
<221> NAME/KEY: MISC_FEATURE
<222> LOCATION: (1)..(29)
<223> OTHER INFORMATION: linker domain L1

<400> SEQUENCE: 4

Gly Ala Ser Ser Ala Gly Asn Thr Asn Ser Gly Gly Ser Thr Thr Thr
1               5                   10                  15

Ile Thr Asn Asn Asn Ser Gly Thr Asn Ser Ser Ser Thr
            20                  25

<210> SEQ ID NO 5
<211> LENGTH: 31
<212> TYPE: PRT
<213> ORGANISM: Saccharomyces cerevisiae
<220> FEATURE:
<221> NAME/KEY: MISC_FEATURE
<222> LOCATION: (1)..(31)
<223> OTHER INFORMATION: linker domain L2

<400> SEQUENCE: 5

Gly Ser Ala Ser Ser Thr Asn Ser Gly Gly Ser Asn Asn Ser Ala Ser
1               5                   10                  15

Thr Thr Pro Thr Thr Ser Val Thr Pro Ala Lys Pro Thr Ser Gln
            20                  25                  30

<210> SEQ ID NO 6
<211> LENGTH: 30
<212> TYPE: PRT
<213> ORGANISM: Saccharomyces cerevisiae
<220> FEATURE:
<221> NAME/KEY: MISC_FEATURE
<222> LOCATION: (1)..(30)
<223> OTHER INFORMATION: Linker domain L3

<400> SEQUENCE: 6

Gln Ser Ala Ala Ala Ser Asn Pro Ser Thr Gly Ser Gly Ser Thr Ala
1               5                   10                  15

Thr Asn Asn Ser Asn Ser Thr Ser Ser Asn Ser Asn Ala Ser
            20                  25                  30

<210> SEQ ID NO 7
<211> LENGTH: 20
<212> TYPE: PRT
<213> ORGANISM: Saccharomyces cerevisiae
<220> FEATURE:
<221> NAME/KEY: MISC_FEATURE
<222> LOCATION: (1)..(20)
<223> OTHER INFORMATION: signal sequence

<400> SEQUENCE: 7

Met Pro Met Gly Ser Leu Gln Pro Leu Ala Thr Leu Tyr Leu Leu Gly
1               5                   10                  15

Met Leu Val Ala
    20